US009969785B2

(12) United States Patent
Fallon et al.

(10) Patent No.: US 9,969,785 B2
(45) Date of Patent: May 15, 2018

(54) BIGLYCAN MUTANTS AND RELATED THERAPEUTICS AND METHODS OF USE

(75) Inventors: Justin R. Fallon, Providence, RI (US); Alison R. Amenta, Pawtucket, RI (US); Beth A. McKechnie, North Attleboro, MA (US); Michelle Dechene, Providence, RI (US); Atilgan Yilmaz, Providence, RI (US)

(73) Assignee: Brown University, Providence, RI (US)

( * ) Notice: Subject to any disclaimer, the term of this patent is extended or adjusted under 35 U.S.C. 154(b) by 0 days. days.

(21) Appl. No.: 13/109,558

(22) Filed: May 17, 2011

(65) Prior Publication Data

US 2012/0004178 A1 Jan. 5, 2012

Related U.S. Application Data

(60) Provisional application No. 61/345,557, filed on May 17, 2010.

(51) Int. Cl.
A61K 38/00 (2006.01)
A61K 31/56 (2006.01)
C07K 14/47 (2006.01)

(52) U.S. Cl.
CPC .......... C07K 14/4725 (2013.01); A61K 38/00 (2013.01)

(58) Field of Classification Search
None
See application file for complete search history.

(56) References Cited

U.S. PATENT DOCUMENTS

| | | | |
|---|---|---|---|
| 5,340,934 A | 8/1994 | Termine et al. | |
| 5,654,270 A | 8/1997 | Ruoslahti | |
| 5,705,609 A | 1/1998 | Ruoslahti et al. | |
| 6,864,236 B1 | 3/2005 | Fallon et al. | |
| 7,335,637 B2 | 2/2008 | Fallon et al. | |
| 7,612,038 B2 | 11/2009 | Fallon et al. | |
| 7,759,314 B2 | 7/2010 | Fallon et al. | |
| 7,816,322 B2 | 10/2010 | Fallon et al. | |
| 8,138,154 B2 | 3/2012 | Fallon et al. | |
| 8,367,619 B2 * | 2/2013 | Wight et al. | 514/21.2 |
| 8,822,418 B2 | 9/2014 | Fallon et al. | |
| 2004/0063627 A1 | 4/2004 | Fallon et al. | |
| 2005/0059580 A1 | 3/2005 | Fallon et al. | |
| 2008/0274966 A1 | 11/2008 | Fallon et al. | |
| 2010/0130405 A1 | 5/2010 | Fallon et al. | |
| 2011/0053854 A1 | 3/2011 | Fallon et al. | |
| 2011/0183910 A1 | 7/2011 | Fallon et al. | |
| 2012/0245095 A1 | 9/2012 | Fallon et al. | |
| 2014/0213523 A1 | 7/2014 | Fallon et al. | |

FOREIGN PATENT DOCUMENTS

| | | |
|---|---|---|
| EP | 0 686 397 A2 | 4/1995 |
| WO | WO-93/10808 A1 | 6/1993 |
| WO | WO-95/13298 A1 | 5/1995 |
| WO | WO-00/54801 | 9/2000 |
| WO | WO-0125461 A1 | 4/2001 |
| WO | WO 2001/036475 | 5/2001 |
| WO | WO 2003/015615 | 1/2003 |
| WO | WO-2003/070195 | 2/2003 |
| WO | WO 2003/070195 | 8/2003 |
| WO | WO 2007/123848 | 11/2007 |
| WO | WO 2008/100789 | 8/2008 |
| WO | WO-2011/146480 A1 | 11/2011 |

OTHER PUBLICATIONS

Hwang et al., "Retrovirally Mediated Overexpression of Gylycosaminoglycan-Deficient Biglycan in Arterial Smooth Muscle Cells Induces Tropoelastin Synthesis and Elastic Fiber Formation in Vitro and in Neointimae after Vascular Injury", Am J. Pathol. 143(6):1919-1928 (2008).
Amenta et al., "Biglycan Recruits Utrophin to the Sarcolemma and Counters Dystrophic Pathology in MDX Mice," Proc Natl. Acad. Sci. USA, 108(2):762-767 (2011).
Ameye, "Mice Deficient in Small Leucine-Rich Proteoglycans: Novel In Vivo Models for Osteoporosis, Osteoarthritis, Ehlers-Danlos Syndrome, Muscular Dystrophy, and Corneal Diseases," Glycobiology, 12(9):107R-116R (2002).
Bianco et al., "Expression and Localization of the Two Small Proteoglycans Biglycan and Decorin in Developing Human Skeletal and Non-Skeletal Tissues," J. Histochem. Cytochem., 38(11):1549-1563 (1990).
Bowe et al., "The Small Leucine-Rich Repeat Proteoglycan Biglycan Binds to α-Dystroglycan and is Upregulated in Dystrophic Muscle," J. Cell Biol., 148(4):801-810 (2000).
Brandan et al., "Novel Regulatory Mechanisms for the Proteoglycans Decorin and Biglycan During Muscle Formation and Muscular Dystrophy," Matrix Biol., 27:700-708 (2008).
Casar et al., "Transient Up-Regulation of Biglycan During Skeletal Muscle Regeneration: Delayed Fiber Growth Along With Decorin ncrease in Biglycan-Deficient Mice," Dev. Biol., 268:358-371,( 2004).
International Search Report from PCT/US2011/036803, dated Aug. 23, 2011.
Fisher et al. as "Deduced Protein Sequence of Bone Small Proteoglycan I (Biglycan Shows Homology with Proteoglycan II (Decorin) and Several Nonconnective Tissue Proteins in a Variety of Species," J. Biol. Chem., 264(8): 4571-4576 (1996).
Fukuta et al. "Molecular Cloning and Expression of Chick Chondrocyte Chondroitin 6-Sulfotransferase," J. Biol. Chem., 270(31)18575-18580 (1995).
Hildebrand et al., "Interaction of the Small Intestitial Proteoglycans Biglycan, Decorin and Fibromodulin with Transforming Growth Factor β," J. Biochem., 302:527-534 (1994).

(Continued)

Primary Examiner — Olga N Chernyshev
(74) Attorney, Agent, or Firm — Foley Hoag LLP

(57) ABSTRACT

The present disclosure provides compositions and methods for treating diseases or conditions associated with an abnormal level or activity of biglycan; disorders associated with an unstable cytoplasmic membrane, for example, due to an unstable dystrophin associated protein complex (DAPC); disorders associated with abnormal synapses or neuromuscular junctions, including those resulting from an abnormal MuSK activation or acetylcholine receptor (AChR) aggregation. Examples of diseases include muscular dystrophies, such as Duchenne's Muscular Dystrophy, Becker's Muscular Dystrophy, neuromuscular disorders and neurological disorders.

4 Claims, 20 Drawing Sheets

(56) References Cited

OTHER PUBLICATIONS

Hocking et al., "Eukaryotic Expression of Recombinant Biglycan; Post-Translational Processing and the Importance of Secondary Structure for Biological Activity," *J. Biol. Chem.* 271(32):19571-19577 (1996).
Hocking et al., "Leucine-Rich Repeat Glycoproteins of the Extracellular Matrix," *Matrix Biol.*, 17:1-19 (1998).
Kobe & Deisenhofer, "The Leucine-Rich Repeat: a Versatile Binding Motif," *Trends Biochem. Sci.*, 19:415-421 (1994).
Kresse et al., "Different Usage of the Glycosaminoglycan Attachment Sites of Biglycan," *J. Biol. Chem.*, 276(16):13411-13416 (2001).
Lechner et al., "Developmental Regulation of Biglycan Expression in Muscle and Tendon," *Muscle Nerve*, 34:347-355 (2006).
Mercado et al. "Biglycan Regulates the Expression and Sarcolemmal Localization of Dystrobrevin, Syntrophin, and nNOS," *The FASEB Journal*, 20:E1075-E1085 (2006).
Moreth et al., "The Proteoglycan Biglycan Regulates Expression of the B Cell Chemoattractant CXCL13 and Aggravates Murine Lupus Nephritis," *J. Clin. Invest.*, 120(12):4251-4272 (2010).
Nastuk et al., "Expression Cloning and Characterization of NSIST, a Novel Sulfotransferase Expressed by a Subset of Neurons and Postsynaptic Targets," *J. Neuroscience*, 18(18)7167-7177 (1998).
O'Brien et al., "Smooth Muscle Cell Biglycan Overexpression Results in Increased Lipoprotein Retention on Extracellular Matrix: Implications for the Retention of Lipoproteins in Atherosclerosis," *Atherosclerosis*, 177:29-35 (2004).
Peat et al., "Exclusion of Biglycan Mutations in a Cohort of Patients With Neuromuscular Disorders," *Neuromuscul Disord.*, 18(8):606-609 (2008).
Rafii et al, "Biglycan Binds to α- and γ- Sarcoglycan and Regulates Their Expression During Development," *J. Cell Physiol.*, 209(2):439-447 (2006).
Rühland et al., The Glycosaminoglycan Chain of Decorin Plays an Important Role in Collagen Fibril Formation at Early Stages of Fibrillogenesis, *The FEBS Journal*, 274:4246-4255 (2007).
Schaefer et al., "Biological Functions of the Small Leucine-Rich Proteoglycans: From Genetics to Signal Transduction," *J. Biol. Chem.*, 283(31):21305-21309 (2008).
Schaefer et al., "The Matrix Component Biglycan is Proinflammatory and Signals Through Toll-Like Receptors 4 and 2 in Macrophages," *J. Clin. Invest.*, 115(8):2223-2233 (2005).
Scott et al., "Crystal Structure of the Biglycan Dimer and Evidence That Dimerization Is Essential for Folding and Stability of Class I Small Leucine-Rich Repeat Proteoglycans," *J. Biol. Chem.*, 281(19):13324-13332 (2006).
Wilberg et al., "Biglycan and Decorin Bind Close to the N-terminal Region of the Collagen VI Triple Helix," *J. Biol. Chem.*, 276(22):18947-18952 (2001).
Xu et al., "Targeted Disruption of the Biglycan Gene Leads to an Osteoporosis-Like Phenotype in Mice," *Nature Genetics*, 20:78-82 (1998).
Athanasopoulos et al., "Recombinant adeno-associated viral (rAAV) vectors as therapeutic tools for Duchenne muscular dystrophy (DMD)," Gene Therapy 11:S109-S121 (2004).
Balaban et al., "Corticosterois treatment and functional improvement in Duchenne muscular dystrophy: long-term effect," American Journal of Physical Medicine & Rehabilitation / Assoc. of AcAdemic Physiatrists, 84:11 843-850 (2005).
Bonaldo et al., "Collagen VI deficiency induces early onset myopathy in the mouse: an animal model for Bethlem myopathy," Human Molecular Genetics 7:13 2134-2140 (1998).
Brown. "Hybridization Analysis of DNA Blots," Unit 2.10, Current Protocols in Molecular Biology, John Wiley & Sons (2003).
Chan, Yiu-mo et al., "Molecular Organization of Sarcoglycan Complex in Mouse Myotubes in Culture." J. Cell Bio. 143, 2033-2044 (Dec. 28, 1998).

Coral-Vasquez, R. et al. Disruption of the Sarcoglycan-Sarcospan Complex in Vascular Smooth Muscle: A Novel Mechanism for Cardiomyopathy and Muscular Dystrophy. Cell 98, 465-74 (1999).
Crosbie, Rachelle H. et al. Membrane Targeting and Stabilizatoin of Sarcospan is Mediated by the Saroglycan Subcomplex. J. Cell. Biol. 145, 159-165 (Apr. 5, 1999).
Ervasti et al., A Role for the Dystrophin-Glycoprotein Complex as a Transmembrane Linker between Laminin and Actin. J. Cell Biol. 122, 809-823 (Aug. 1993).
Farooqi et al., Effects of Recombinant Leptin Therapy in a Child with Congenital Leptin Deficiency, N. E. Journal of Medicine, 341: 879-884 (1999).
Ferri, R. T. et al. A Role for Biglycan in Agrin-Induced Postsynaptic Differentiation. Society for Neuroscience Abstracts 26 (2000) [Abstract Only].
Gee, Stephen H. et al. Dystroglycan-a, a Dystrophin-Associated Glycoprotein, is a Functional Agrin Receptor. Cell 77, 675-686 (Jun. 3, 1994).
Gregorevic et al., "Gene therapy for muscular dystrophy—a review of promising progress," Expert Opin Biol Ther., 3(5) 803-14 (2003).
Guglieri, et al., "Molecular Etiopathogenesis of Limb Girdle Muscular and Congenital Muscular Dystrophies: Boundaries and Contiguities," Clinica Chimica Acta 361 (2005) 54-79.
Hammond et al., "PRO-051, an antisense oligonucleotide for the potential treatment of Duchenne muscular dystrophy" Current Opinion in Molecular Therapeutics, 12:4 478-486 (2010).
Hasenohrl et al., "Facilitation of learning following injection of the chondroitin sulfate proteoglycan biglycan into the vicinity of the nucleus basalis magnocellularis," Behavioural Brain Research, 70:59-67 (1995).
Hoch, Werner. Formation of the Neuromuscular Junction: Agrin and its unusual receptors. Eur. J. Biochem. 265, 1-10(1999).
Holt, Kathleen H. et al. Functional Rescue of the Sarcoglycan Complex in the BIO 14.6 Hamster Using S-Sarcoglycan Gene Transfer. Mol. Cell 1, 841-848 (May 1998).
Ibraghimov-Beslrovanaya et al. Human Dystroglycan: Skeletal Muscle cDNA, Genomic Structure, Origin of Tissue Specific Isoforms and Chromosomal Localization. Hum. Mol. Genet. 2, 1651-1657 (1993).
Iozzo, R. Matrix Proteoglycans: From Molecular Design to Cellular Function. Ann. Rev. Biochem. 67, 609-652 (1998).
Jarvelainen, Hannu T. et al. Differential Expression of Small Chondroitin/Dermatan Sulfate Proteoglycans, PG-I/Biglycan and PG-II/Decorin, by Vascular Smooth Muscle and Endothelial Cells in Culture. J. Biol. Chem. 266, 23274-23281 (Dec. 5, 1991).
Junghans, Ulrich et al. Purification of a Meningeal Cell-derived Chondroitin Sulphate Proteoglycan with Neurotrophic Activity for Brain Neurons and its Identification as Biglycan. Euro. J. Neurosci. 7, 2341-2350 (1995).
Khan, M.A. "Corticosteroid therapy in Duchenne muscular dystrophy" Journal of the Neurological Sciences, 120:1, 8-14 (1993).
Khurana, T. S. et al. Interaction of ARIA, a Neuregulin, with the Dystroglycan / Sarcoglycan Complex in Skeletal Muscle. Mol. Cell. Biol. 7, 314 (1996).
King, W.M. et al. "Orthopedic outcomes of long-term daily corticosteroid treatment in Duchenne muscular dystrophy" Neurology, 68(19): 1607-1613 (2007).
Krishnan, P. et al., "Distinct Secondary Structures of the Leucine-rich Repeat Proteoglycans Decorin and Biglycan." J. Biol. Chem. 274, 10945-50 (1999).
Krivickas, L.S. et al. "Single muscle fiber contractile properties in adults with muscular dystrophy treated with MYO-029" Muscle & Nerve, 39:1 309 (2009).
Lamandé et al., "Reduced collagen VI causes Bethlem myopathy: a heterozygous COL6A1 nonsense mutation results in mRNA decay and functional haploinsufficiency," Human Molecular Genetics, 7:6 (981-989 (1998).
Lampe et al., "Collagen VI Related Muscle Disorders," J. Med. Genet. 2005;42;673-685.
Langton, et al., "Localization of the Functional Domains of Human Tissue Inhibitor of Metalloproteinases-3 and the Effects of a Sorsby's Fundus Dystropy Mutation," The Journal of Biological Chemistry, 273:16778-16781 (1998).

(56) References Cited

OTHER PUBLICATIONS

Matthews D.J. et al. "Use of corticosteroids in a population-based cohort of boys with Duchenne and Becker muscular dystrophy", Journal of Child Neurology, 25:11, 1319-1324 (2010).

O'Toole et al., "Alternative splicing of agrin regulates its binding to heparin, a-dystroglycan, and the cell surface," Proc. Natl. Acad. Sci 93: 7369-7374 (1996).

Rafii et al., "Interactions of the Proteoglycan Biglycan with the Dystrophin Associated Protein Complex and its Roles in Muscular Dystrophy and Synaptogenesis," (Abstract from 40th American Society for Cell Biology Annual Meeting) Molecular Biology of the Cell, 11:146a (2000).

Sakamoto, Aiji et al. Both hypertrophic and dilated cardiomyopathies are caused by mutation of the same gene, S-sarcoglycan, in hamster. An animal model of disrupted dystrophin-associated glycoprotein complex. PNAS 94: 13873-13878 (Dec. 1997).

Smythe et al., "Altered caveolin-3 expression disrupts PI(3) kinase signaling leading to death of cultured muscle cells," Experimental Cell Research, 312:15 2816-2825 (2006).

Speer et al., "Evidence for locus heterogeneity in the Bethlem myopathy and linkage to 2q37," Hum. Mol. Genet. 1996, 5(7):1043-6.

Spence et al., "Muscular dystrophies, the cytoskeleton and cell adhesion," BioEssays 24:542-552, 2002.

Tomoyasu, Hiroshi et al. Identification of haemopoietic biglycan in hyperplastic thymus associated with myasthenia gravis, J. Neuroimmunology, 89, 59-63 (1998).

Vanegas et al., "Ullrich scleroatonic muscular dystrophy is caused by recessive mutations in collagen type VI," PNAS, 98(13):7516-7521 (2001).

Von der Mark et al., "Immunochemistry, genuine size and tissue localization of collagen VI," Eur. J. Biochem. 142(3):493-502, 1984.

Winder, Steven J. The complexitites of dystroglycan. Trends in Biochem. Sci. 26, 118-124 (2001).

Fadic et al., Increase in decorin and biglycan in Duchenne Muscular Dystrophy: role of fibroblasts as cell source of these proteoglycans in the disease. J. Cell. Mol. Med. 10:3, 758-769 (Jul. 3, 2006).

Amenta, "Biglycan at synapses, the sarcolemma and as a potential therapeutic for Duchenne Muscular Dystrophy," PhD Thesis, 2007, Dept. of neuroscience, Brown University, Providence, Rhode Island USA.

Davies: "Utrophin and therapy of DMP PPMD Annual Conf. Acknowledgements," Annual Connect Conference, XP0551523, Retrieved from the Internet: ULR:http://www.parentprojectmd.org/site/DocServer/DaviesPPMD2007.pdf.docID=2321 [retrieved on Nov. 7, 2014] p. 16-24.

Gramolini et al., "Muscle and Neural Isoforms of Agrin Increase Utrophin Expression in Cultured Myotubes via a Transcriptional Regulatory Mechanism," Journal of Biological Chemistry, 272(2): 736-743 (1998).

Miura et al., "Utrophin upregulation for treating Duchenne or Becker muscular dystrophy: how close are we?" Trends in Molecular Medicine, Elsevier Current Trends, GB, 12(3) 122-129 (2006), XP028058695, ISSN: 1471-4914, DOI.

Nguyen, et al., "Utrophin, the autosomal homologue of dystrophin, is widely-expressed and membrane-associated in cultured cell lines," FEBS Letters, 313(1) 19-22 (1992).

Buxbaum et al., "Processing of Alzheimer Beta/A4 Amyloid Precursor Protein: Modulation by Agents that Regulate Protein Phosphorylation," Proc. Nat. Acad. Sci., 87:6003-6006 (1990).

Yoshida et al., "Bidirectional Signaling Between Sarcoglycans and the Integrin Adhesion System in Cultured L6 Myocytes," The Journal of Biological Chemistry, 273(3):1583-1590 (1998).

* cited by examiner

Figure 2

```
TORPEDO    IQAIEFEDL (SEQ ID NO: 1)    LGLGFNEIR (SEQ ID NO: 2)
           |||||  |||                  ||||  | ||
HUMAN      IQAIELEDL (SEQ ID NO: 4)    LGLGHNQIR (SEQ ID NO: 5)
           241       249               258       266

TORPEDO    TSYHGISLFNNPVNYWDVL (SEQ ID NO: 3)
             |||||||||| || |
HUMAN      AYYNGISLFNNPVPYWEVQ (SEQ ID NO: 6)
           330                 348
```

Biglycan Structure

- GAG addition sites
- Y – N-linked carbohydrate

Figure 9. Bioactivity of NG and S5A-S10A biglycan in a cell culture bioassay.
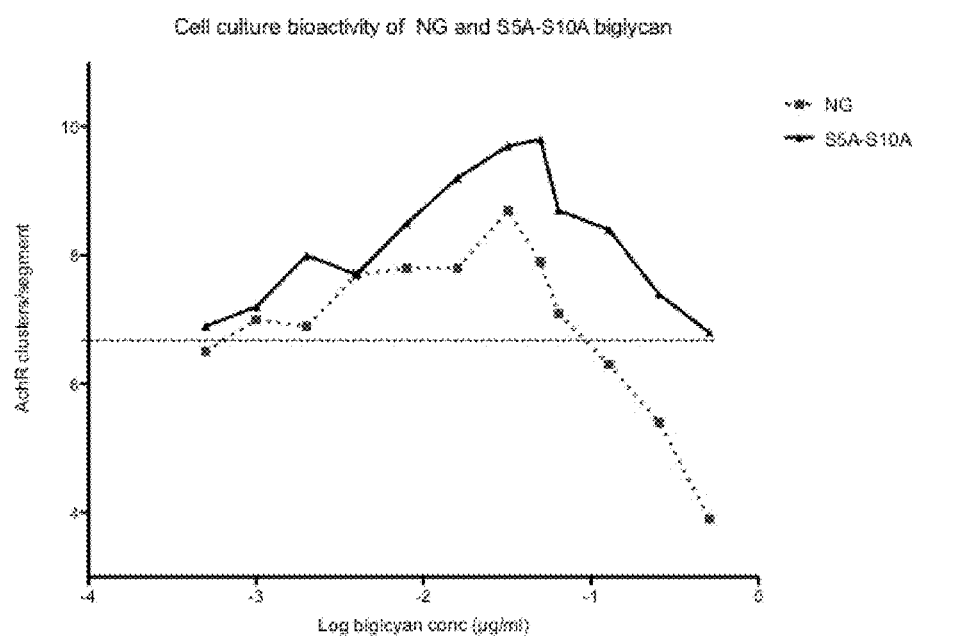
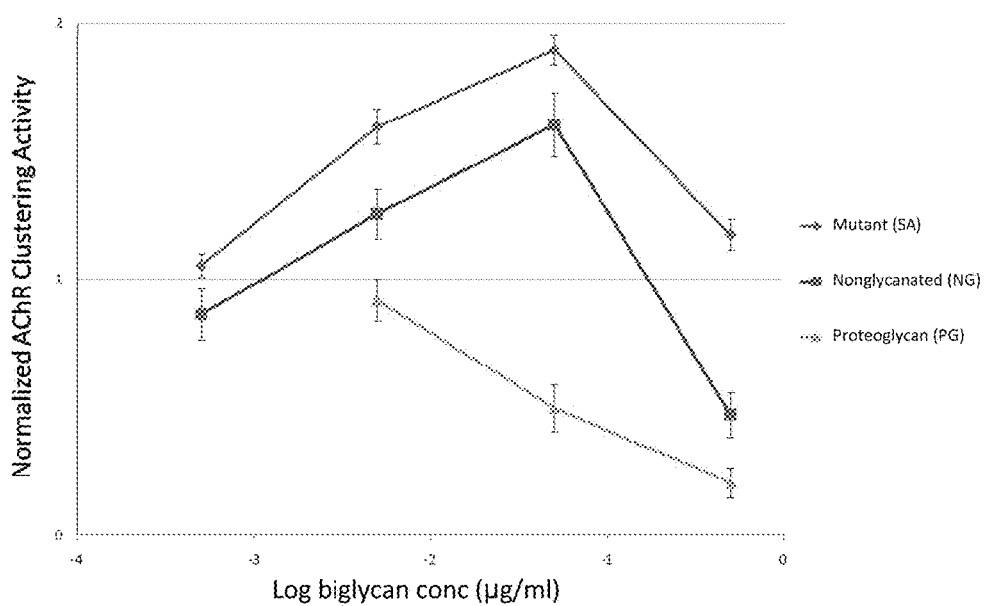

(a) 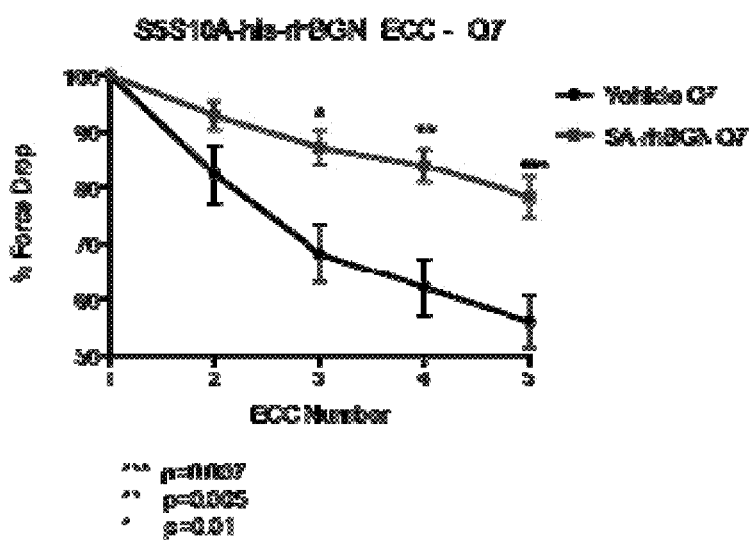
(b) 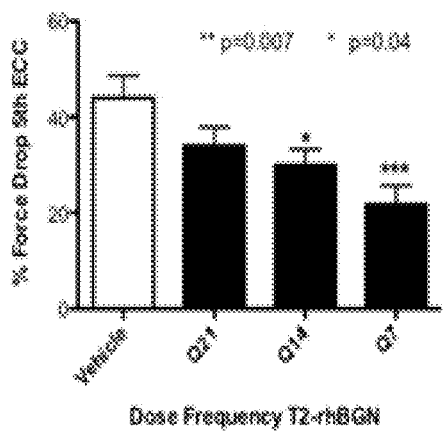
(c) 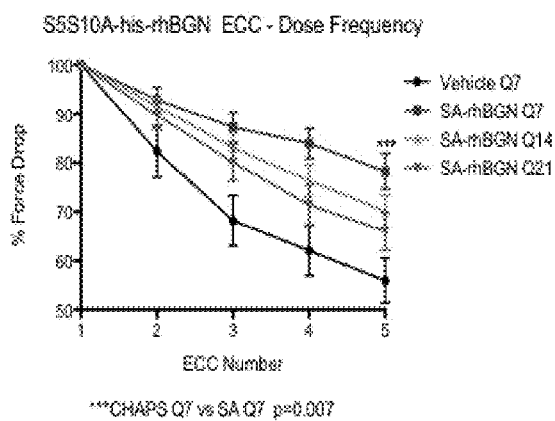
Figure 11.

Improved muscle health in mdx mice injected with SA-rhBGN

Figure 13
A.
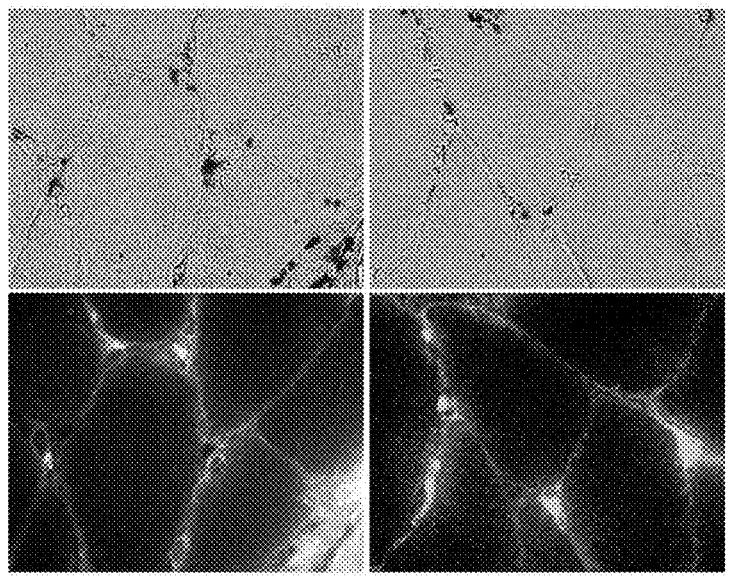
B.
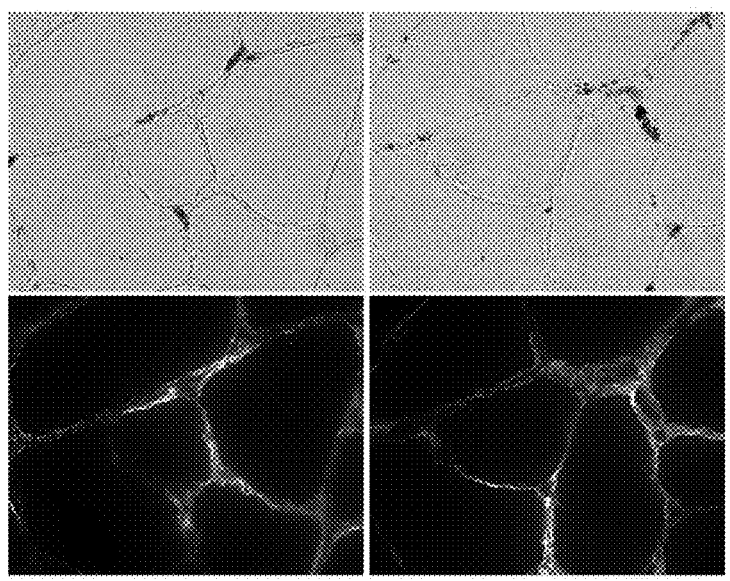

Figure 14

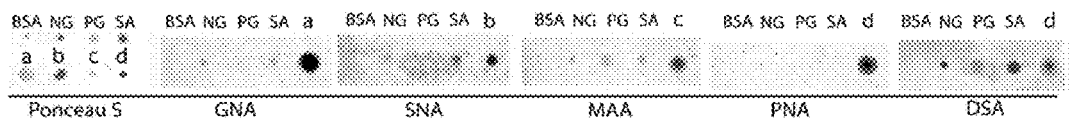

| Lectin | Binding Preference | Proteoglycan (PG) | Non-glycanated (NG) | Mutant (SA) |
|---|---|---|---|---|
| GNA (Galanthus nivalis agglutinin) | Terminal Man; (1-3), (1-6) or (1-2) | - | + | + |
| SNA (Sambucus nigra agglutinin) | Sialic acid linked (2-6) to Gal or GalNAc | - | + | + |
| MAA (Maackia amurensis agglutinin) | Sialic acid linked (2-3) to Gal | + | + | + |
| PNA (Peanut agglutinin) | Galβ(1-3)GalNAc | - | - | - |
| DSA (Datura stramonium agglutinin) | Galβ(1-4)GlcNAc or terminal GlcNAc | + | + | + |

Figure 15

| Nonglycanated (NG) Biglycan | | |
|---|---|---|
| Sequon | Peptide Position | Peptide Sequence[a] |
| $Asn^{270}$ | 267-280 | (R)MIEN@GSLSFLPTLR(E) |
| $Asn^{311}$ | 301-314 | (K)LLQVVYLHSNN@ITK(V) |

| Mutant (SA) Biglycan | | |
|---|---|---|
| Sequon | Peptide Position | Peptide Sequence[a] |
| $Asn^{270}$ | 267-280 | (R)MIEN@GSLSFLPTLR(E) |
| $Asn^{311}$ | 301-314 | (K)LLQVVYLHSNN@ITK(V) |

[a]An @ indicates the site of N-glycosylation

Sequon → Asn-X-Ser or Asn-X-Thr

SEQUENCE LISTING

<160> NUMBER OF SEQ ID NOS: 11

<210> SEQ ID NO 1
<211> LENGTH: 9
<212> TYPE: PRT
<213> ORGANISM: Torpedo californica

<400> SEQUENCE: 1

Ile Gln Ala Ile Glu Phe Glu Asp Leu
1               5

<210> SEQ ID NO 2
<211> LENGTH: 9
<212> TYPE: PRT
<213> ORGANISM: Torpedo californica

<400> SEQUENCE: 2

Leu Gly Leu Gly Phe Asn Glu Ile Arg
1               5

<210> SEQ ID NO 3
<211> LENGTH: 19
<212> TYPE: PRT
<213> ORGANISM: Torpedo californica

<400> SEQUENCE: 3

Thr Ser Tyr His Gly Ile Ser Leu Phe Asn Asn Pro Val Asn Tyr Trp
1               5                   10                  15

Asp Val Leu

<210> SEQ ID NO 4
<211> LENGTH: 9
<212> TYPE: PRT
<213> ORGANISM: Homo sapiens

<400> SEQUENCE: 4

Ile Gln Ala Ile Glu Leu Glu Asp Leu
1               5

<210> SEQ ID NO 5
<211> LENGTH: 9
<212> TYPE: PRT
<213> ORGANISM: Homo sapiens

<400> SEQUENCE: 5

Leu Gly Leu Gly His Asn Gln Ile Arg
1               5

<210> SEQ ID NO 6
<211> LENGTH: 19
<212> TYPE: PRT
<213> ORGANISM: Homo sapiens

<400> SEQUENCE: 6

Ala Tyr Tyr Asn Gly Ile Ser Leu Phe Asn Asn Pro Val Pro Tyr Trp
1               5                   10                  15

Glu Val Gln

<210> SEQ ID NO 7
<211> LENGTH: 1685
<212> TYPE: DNA
<213> ORGANISM: Homo sapiens

<400> SEQUENCE: 7

```
gagtagctgc tttcggtccg ccggacacac cggacagata gacgtgcgga cggcccacca    60
ccccagcccg ccaactagtc agcctgcgcc tggcgcctcc cctctccagg tccatccgcc   120
atgtggcccc tgtggcgcct cgtgtctctg ctggccctga gccaggccct gccctttgag   180
cagagaggct tctgggactt caccctggac gatgggccat tcatgatgaa cgatgaggaa   240
gcttcgggcg ctgacacctc aggcgtcctg gacccggact ctgtcacacc cacctacagc   300
gccatgtgtc ctttcggctg ccactgccac ctgcgggtgg ttcagtgctc cgacctgggt   360
ctgaagtctg tgcccaaaga gatctcccct gacaccacgc tgctggacct gcagaacaac   420
gacatctccg agctccgcaa ggatgacttc aagggtctcc agcacctcta cgccctcgtc   480
ctggtgaaca caagatctc caagatccat gagaaggcct tcagcccact gcggaagctg   540
cagaagctct acatctccaa gaaccacctg gtggagatcc cgccaacct acccagctcc   600 ctggtggagc tccgcatcca cgacaaccgc atccgcaagg tgcccaaggg agtgttcagc   660
gggctccgga acatgaactg catcgagatg gcgggaacc cactggagaa cagtggcttt   720
gaacctggag ccttcgatgg cctgaagctc aactacctgc gcatctcaga ggccaagctg   780
actggcatcc ccaaagacct ccctgagacc ctgaatgaac tccacctaga ccacaacaaa   840
atccaggcca tcgaactgga ggacctgctt cgctactcca agctgtacag gctgggccta   900
ggccacaacc agatcaggat gatcgagaac gggagcctga gcttcctgcc caccctccgg   960
gagctccact tggacaacaa caagttggcc agggtgccct cagggctccc agacctcaag  1020
ctcctccagg tggtctatct gcactccaac aacatcacca agtgggtgt caacgacttc  1080 tgtcccatgg gcttcggggt gaagcgggcc tactacaacg gcatcagcct cttcaacaac  1140
cccgtgccct actgggaggt gcagccggcc actttccgct gcgtcactga ccgcctggcc  1200
atccagtttg gcaactacaa aaagtagagg cagctgcagc caccgcgggg cctcagtggg  1260
ggtctctggg gaacacagcc agacatcctg atggggaggc agagccagga agctaagcca  1320
gggcccagct gcgtccaacc cagcccccca cctcaggtcc ctgaccccag ctcgatgccc  1380
catcaccgcc tctccctggc tcccaagggt gcaggtgggc gcaaggcccg gcccccatca  1440
catgttccct tggcctcaga gctgcccctg ctctcccacc acagccaccc agaggcaccc  1500
catgaagctt ttttctcgtt cactcccaaa cccaagtgtc caaagctcca gtcctaggag  1560 aacagtccc gggtcagcag ccaggaggcg gtccataaga atggggacag tgggctctgc  1620
cagggctgcc gcacctgtcc agaacaacat gttctgttcc tcctcctcat gcatttccag  1680
ccttg                                                              1685

<210> SEQ ID NO 8
<211> LENGTH: 1104
<212> TYPE: DNA
<213> ORGANISM: Homo sapiens

<400> SEQUENCE: 8
atgtggcccc tgtggcgcct cgtgtctctg ctggccctga gccaggccct gccctttgag    60
cagagaggct tctgggactt caccctggac gatgggccat tcatgatgaa cgatgaggaa   120
gcttcgggcg ctgacacctc aggcgtcctg gacccggact ctgtcacacc cacctacagc   180
gccatgtgtc ctttcggctg ccactgccac ctgcgggtgg ttcagtgctc cgacctgggt   240
ctgaagtctg tgcccaaaga gatctcccct gacaccacgc tgctggacct gcagaacaac   300
gacatctccg agctccgcaa ggatgacttc aagggtctcc agcacctcta cgccctcgtc   360
```

```
ctggtgaaca acaagatctc caagatccat gagaaggcct tcagcccact gcggaagctg    420
cagaagctct acatctccaa gaaccacctg gtggagatcc cgcccaacct acccagctcc    480
ctggtggagc tccgcatcca cgacaaccgc atccgcaagg tgcccaaggg agtgttcagc    540
gggctccgga acatgaactg catcgagatg ggcgggaacc cactggagaa cagtggcttt    600
gaacctggag ccttcgatgg cctgaagctc aactacctgc gcatctcaga ggccaagctg    660
actggcatcc ccaaagacct ccctgagacc ctgaatgaac tccacctaga ccacaacaaa    720
atccaggcca tcgaactgga ggacctgctt cgctactcca agctgtacag gctgggccta    780
ggccacaacc agatcaggat gatcgagaac gggagcctga gcttcctgcc caccctccgg    840
gagctccact tggacaacaa caagttggcc agggtgccct cagggctccc agacctcaag    900
ctcctccagg tggtctatct gcactccaac aacatcacca agtgggtgt caacgacttc    960 tgtcccatgg gcttcggggt gaagcgggcc tactacaacg gcatcagcct cttcaacaac   1020
cccgtgccct actgggaggt gcagccggcc actttccgct gcgtcactga ccgcctggcc   1080
atccagtttg gcaactacaa aaag                                           1104
```

<210> SEQ ID NO 9
<211> LENGTH: 368
<212> TYPE: PRT
<213> ORGANISM: Homo sapiens

<400> SEQUENCE: 9

```
Met Trp Pro Leu Trp Arg Leu Val Ser Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240
```

```
Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365

<210> SEQ ID NO 10
<211> LENGTH: 368
<212> TYPE: PRT
<213> ORGANISM: Artificial Sequence
<220> FEATURE:
<223> OTHER INFORMATION: mutant of Homo sapiens biglycan
<220> FEATURE:
<221> NAME/KEY: MISC_FEATURE
<222> LOCATION: 42
<223> OTHER INFORMATION: Xaa can be absent or can be any amino acid
      except Ser or Thr
<220> FEATURE:
<221> NAME/KEY: MISC_FEATURE
<222> LOCATION: 47
<223> OTHER INFORMATION: Xaa can be absent or can be any amino acid
      except Ser or Thr

<400> SEQUENCE: 10

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Xaa Gly Ala Asp Thr Xaa Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190
```

```
Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365

<210> SEQ ID NO 11
<211> LENGTH: 368
<212> TYPE: PRT
<213> ORGANISM: Artificial Sequence
<220> FEATURE:
<223> OTHER INFORMATION: mutant of Homo sapiens biglycan

<400> SEQUENCE: 11

Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ala Gly Ala Asp Thr Ala Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190
```

```
Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
        210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
            245                 250                 255

Arg Leu Gly Leu Gly His Asn Gln Ile Arg Met Ile Glu Asn Gly Ser
        260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
        290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365
```

BIGLYCAN MUTANTS AND RELATED THERAPEUTICS AND METHODS OF USE

CROSS-REFERENCE TO RELATED APPLICATION

This application claims the benefit of U.S. Provisional Application No. 61/345,557, filed May 17, 2010. The entire teachings of the referenced application are expressly incorporated herein by reference.

GOVERNMENT GRANTS

This invention was made with government support under HD023924, NS064295 and AR055878 awarded by National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on May 17, 2011, is named BURF012101.txt and is 14,956 bytes in size.

BACKGROUND OF THE INVENTION

The dystrophin-associated protein complex (DAPC) links the cytoskeleton to the extracellular matrix and is necessary for maintaining the integrity of the muscle cell/plasma membrane. The core DAPC consists of the cytoskeletal scaffolding molecule dystrophin and the dystroglycan and sarcoglycan transmembrane subcomplexes. The DAPC also serves to localize key signaling molecules to the cell surface, at least in part through its associated syntrophins (Brenman, et al. (1996) *Cell.* 84: 757-767; Bredt, et al. (1998), *Proc Natl Acad Sci USA.* 95: 14592). Mutations in either dystrophin or any of the sarcoglycans result in muscular dystrophies characterized by breakdown of the muscle cell membrane, loss of myofibers, and fibrosis (Hoffman, et al. 1987. *Cell.* 51: 919; Straub, and Campbell (1997) *Curr Opin Neurol.* 10: 168). Moreover, mutations in the extracellular matrix protein laminin-α2, which associates with the DAPC on the cell surface, is the basis of a major congenital muscular dystrophy (Helbling-Leclerc, et al. (1995) *Nat Genet.* 11: 216).

The α-/β-dystroglycan subcomplex forms a critical structural link in the DAPC. The transmembrane β-dystroglycan and the wholly extracellular α-dystroglycan arise by proteolytic cleavage of a common precursor (Ibraghimov, et al. (1992) *Nature* 355: 696; Bowe, et al. (1994) *Neuron* 12: 1173). The cytoplasmic tail of β-dystroglycan binds dystrophin, while the highly glycosylated, mucin-like α-dystroglycan binds to several ECM elements including agrin, laminin, and perlecan (Ervasti and Campbell, (1993) *J Cell Biol.* 122: 809; Bowe, et al. (1994) *Neuron.* 12: 1173; Gee, et al. (1994) *Cell* 77: 675; Hemler, (1999) *Cell* 97: 543). This binding to matrix proteins appears to be essential for assembly of basal lamina, since mice deficient in dystroglycan fail to form these structures and die very early in development (Henry, M. D. and K. P. Campbell. 1998. *Cell.* 95: 859). β-Dystroglycan can bind the signaling adapter molecule Grb2 and associates indirectly with p125FAK (Yang, et al. (1995) *J. Biol. Chem.* 270: 11711; Cavaldesi, et al. (1999), *J. Neurochem.* 72: 01648). Although the significance of these associations remains unknown, these binding properties suggest that dystroglycan may also serve to localize signaling molecules to the cell surface.

Several lines of evidence suggest that dystroglycan may also function in neuromuscular junction formation, in particular, in postsynaptic differentiation. For purposes of clarity, the components of the neuromuscular junction are summarized here. The major structural features of the neuromuscular junction (NMJ) or nerve-muscle synapse are the pre- and post-synaptic specializations of the motor neuron and muscle, respectively, the intervening synaptic basal lamina, and the specialized Schwann cell cap (Salpeter, et al (1987) *The Vertebrate Neuromuscular Junction.* New York, Alan R. Liss.). The presynaptic apparatus is marked by ordered arrays of synaptic vesicles, a subset of which are poised to fuse with the plasma membrane at the active zones, and release acetylcholine that is recognized by acetylcholine receptors (AChRs) on the muscle, and ultimately results in electrical activation and contraction of the muscle (Heuser, et al (1981) *J. Cell Biol.* 88: 564) Immediately across the 50 nm synaptic cleft from these zones are the crests of the postjunctional folds. These crests bristle with AChRs, which can reach densities of >10,000 molecules/$\mu m^2$ (Fertuck, et al (1976) *J. Cell. Biol.* 69: 144). The localized and tightly regulated secretion of acetylcholine into the narrow synaptic cleft, coupled with the high AChR density in the postsynaptic membrane, ensures rapid and reliable synaptic transmission between neuron and muscle. Perturbations of these specializations, such as the decrease in the number of functional AChRs seen in myasthenia gravis, can lead to debilitating and often fatal clinical outcomes (Oosterhuis, et al (1992) *Neurology & Neurosurgery* 5: 638).

The synaptic basal lamina (SBL) is interposed between the pre- and post-synaptic membranes and contains molecules important for the structure, function, and regulation of the neuromuscular junction (Bowe, M. A & Fallon, J. R., (1995) *Ann. Rev. Neurosci.* 18: 443; Sanes, et al. (1999) *Ann. Rev. Neurosci.* 22: 389). It consists of a distinct set of extracellular matrix molecules including specialized laminins, proteoglycans and collagens (Hall, et al (1993) *Neuron* 10: (Suppl.) 99). The SBL also contains molecules essential for the regulation of synaptic structure and function including AChE, neuregulins, and agrin. The SBL thus serves both as a specialized structure for maintaining the localized differentiation of the synapse as well as a repository for essential regulatory molecules.

The molecular composition of the postsynaptic membrane is known in considerable detail. As noted above, the most abundant membrane protein is the AChR. The cytosolic AChR associated protein rapsyn (formerly known as the 43 kD protein) is present at stoichiometric levels with the receptor and is likely to form a key link between the cytosolic domain of the AChR and the cytoskeleton (Froehner, et al (1995) *Nature* 377: 195; Gautam, et al. (1995) *Nature* 377: 232). The postsynaptic membrane is also enriched in erbB2-4, some or all of which serve as neuregulin receptors (Altiok, et al. (1995) *EMBO J.* 14: 4258; Zhu, et al. (1995) *EMBO J.* 14: 5842). AChR and other molecules essential for nerve-muscle communication. The cytoskeletal elements can be broadly grouped into two subsets. Dystrophin and utrophin are members of the DAPC, and are linked to the synaptic basal lamina via the transmembrane heteromer α-/β-dystroglycan. The postsynaptic cytoskeleton is also enriched in several focal adhesion-associated molecules including α-actinin, vinculin, talin, paxillin, and filamin (Sanes, et al (1999) *Ann. Rev. Neurosci.* 22: 389). The latter proteins probably communicate, directly or indirectly, with the extracellular matrix through integrins, some of which are enriched at synapses (Martin, et al. (1996) *Dev. Biol.* 174: 125). Actin is associated with both sets of cytoskeletal molecules (Rybakova et al. (1996) *J. Cell Biol.* 135: 661; Amann, et al. (1998) *J. Biol. Chem.* 273: 28419-23; Schoenwaelder et al. (1999) *Curr. Opin. Cell. Biol.* 11: 274). The functions of these specialized sets of proteins are considered below.

α-Dystroglycan binds the synapse organizing molecule agrin (Bowe, et al. (1994) *Neuron.* 12: 1173; Campanelli, et al. (1994) *Cell.* 77: 663; Gee, et al. (1994) *Cell.* 77: 675; Sugiyama, et al. (1994) *Neuron.* 13: 103; O'Toole, et al. (1996) *Proc Natl Acad Sci USA.* 93: 7369) (reviewed in Fallon and Hall, (1994) *Trends Neurosci.* 17: 469), and β-dystroglycan binds to the AChR-associated protein rapsyn (Cartaud, et al. (1998) *J Biol Chem.* 273: 11321). Further, agrin-induced AChR clustering on the postsynaptic membrane is markedly decreased in muscle cells expressing reduced levels of dystroglycan (Montanaro, et al. (1998) *J Neurosci.* 18: 1250). The precise role of dystroglycan in this process is unknown. Currently available evidence suggests that dystroglycan is not part of the primary agrin receptor, but rather may play a structural role in the organization of postsynaptic specializations (Gesemann, et al. (1995) *Biol.* 128: 625; Glass, et al. (1996) *Cell.* 85: 513; Jacobson, et al. (1998) *J Neurosci.* 18: 6340).

Another molecule that plays an important role in neuromuscular junction formation is the tyrosine kinase receptor MuSK, which becomes phosphorylated in response to agrin. However, agrin does not bind to MuSK and it is unclear how agrin stimulates MuSK. The existence of a co-receptor had been suggested. Activation of MuSK by antibody cross-linking is sufficient to induce the clustering of AChRs on cultured myotubes (Xie et al. (1997) *Nat. Biotechnol.* 15:768 and Hopf and Hoch (1998) *J. Biol. Chem.* 273: 6467) and a constitutively active MuSK can induce postsynaptic differentiation in vivo (Jones et al. (1999) *J. Neurosci.* 19:3376). However, MuSK phosphorylation is necessary but not sufficient for agrin-induced AChR clustering.

The realm of dystroglycan function ranges far beyond muscle. As noted above, mice defective in dystroglycan die long before muscle differentiation. In a surprising development, α-dystroglycan in non-muscle cells has been shown to function as a receptor for Lassa Fever and choriomeningitis fever viruses (Cao, W., et al., 1998, *Science.* 282: 2079), and on Schwann cells as a co-receptor for *Mycobacterium leprae* (Rambukkana, et al. (1998) *Science.* 282: 2076). Dystroglycan is also abundant in brain, but its function there is not understood (Gorecki, et al. (1994) *Hum Mol Genet.* 3: 1589; Smalheiser and Kim (1995) *J Biol Chem.* 270: 15425).

α-Dystroglycan is comprised of three known domains. An amino-terminal domain folds into an autonomous globular configuration (Brancaccio, et al. (1995) *Febs Lett.* 368: 139). The middle third of the protein is serine- and threonine-rich, and is highly glycosylated (Brancaccio, et al. (1997) *Eur J Biochem.* 246: 166). Indeed, the core molecular weight of α-dystroglycan is ~68 kDa, but the native molecule migrates on SDS-PAGE as a polydisperse band whose size ranges from 120-190 kDa, depending upon the species and tissue source (Ervasti and Campbell (1993) *J Cell Biol.* 122: 809; Bowe, et al. (1994) *Neuron.* 12: 1173; Gee, et al. (1994) *Cell.* 77: 675; Matsumura, et al. (1997) *J Biol Chem.* 272: 13904). Glycosylation of α-dystroglycan, probably in this middle third, is essential for its laminin- and agrin-binding properties.

It is clear that dystroglycan and the DAPC play crucial roles in a variety of processes in muscle as well as in other tissues. There is a need to develop therapeutic agents and methods which modulate functions of dystroglycan and/or the DAPC.

SUMMARY OF THE INVENTION

In certain embodiments, the present disclosure provides a biglycan-related therapeutic polypeptide, comprising a polypeptide sequence having at least two amino acid residue substitutions at two serine residues of a corresponding biglycan, such that the biglycan-related therapeutic polypeptide does not comprise any glycosaminoglycan (GAG) side chains. In some embodiments, the biglycan-related therapeutic polypeptide comprises an amino acid sequence which is at least 90% identical to SEQ ID NO: 9, or a fragment thereof. In some embodiments, the two serine residues are at positions corresponding to residues 42 and 47 of SEQ ID NO: 9. In some embodiments, the biglycan-related therapeutic polypeptide comprises the amino acid sequence of SEQ ID NO: 10, or a fragment thereof. In some embodiments, the biglycan-related therapeutic polypeptide comprises the amino acid sequence of SEQ ID NO: 11, or a fragment thereof.

In certain embodiments, the biglycan-related therapeutic polypeptide activates muscle specific kinase (MuSK) on the cell. In some embodiments, the biglycan-related therapeutic polypeptide potentiates agrin-induced phosphorylation of MuSK. In some embodiments, the biglycan-related therapeutic polypeptide upregulates utrophin levels. In some embodiments, the biglycan-related therapeutic polypeptide binds to MuSK. In some embodiments, the biglycan-related therapeutic polypeptide binds to a α-sarcoglycan and/or γ-sarcoglycan. In some embodiments, the biglycan-related therapeutic polypeptide induces phosphorylation of sarcoglycans. In some embodiments, the biglycan-related therapeutic polypeptide potentiates agrin-induced clustering of acetylcholine receptors (AChR). In some embodiments, the biglycan-related therapeutic polypeptide comprises one or more LRRs in SEQ ID NO: 9.

In some embodiments, the biglycan-related therapeutic polypeptide comprises an amino acid sequence at least 90% identical to amino acids 38-365 of SEQ ID NO: 9. In some embodiments, the biglycan-related therapeutic polypeptide is encoded by a nucleic acid which hybridizes to SEQ ID NO: 8.

In certain embodiments, the present disclosure provides a pharmaceutical composition comprising: (i) a biglycan-related therapeutic polypeptide; and (ii) a pharmaceutically acceptable carrier.

In certain embodiments, the present disclosure provides a method for stabilizing dystrophin-associated protein complexes (DAPCs) on the surface of a cell, comprising contacting the cell with an effective amount of a biglycan-related therapeutic polypeptide or composition comprising a biglycan-related therapeutic polypeptide.

In certain embodiments, the present disclosure provides a method for activating a postsynaptic membrane of a cell, comprising contacting the cell with an effective amount of a biglycan-related therapeutic polypeptide or composition comprising a biglycan-related therapeutic polypeptide.

In certain embodiments, the present disclosure provides a method for activating MuSK in a cell, comprising contacting the cell with an effective amount of a biglycan-related therapeutic polypeptide or composition comprising a biglycan-related therapeutic polypeptide.

In certain of the above embodiments, the cell is a muscle cell.

In certain embodiments, the present disclosure provides a method for treating a condition associated with an abnormal dystrophin-associated protein complex (DAPC) in cells of a subject, comprising administering to the subject an effective amount of a biglycan-related therapeutic polypeptide or composition comprising a biglycan-related therapeutic polypeptide. For example, the condition may be a muscular dystrophy selected from Duchenne's Muscular Dystrophy, Becker's Muscular Dystrophy, Congenital Muscular Dystrophy, Limb-girdle Muscular Dystrophy, and myotonic dystrophy.

In certain embodiments, the present disclosure provides a method for treating a condition characterized by an abnormal neuromuscular junction or synapse in a subject, comprising administering to the subject an effective amount of a biglycan-related therapeutic polypeptide or composition comprising a biglycan-related therapeutic polypeptide. Such a condition may be a neuromuscular or a neurological disease.

In certain embodiments, the present disclosure provides a method for treating or preventing a condition associated with a collagen VI deficiency, comprising administering to the subject an effective amount of a biglycan-related therapeutic polypeptide or composition comprising a biglycan-related therapeutic polypeptide. The condition associated with a collagen VI deficiency may be Bethlem's myopathy, Ullrich Congenital Muscular Dystrophy, or Sorsby's fundus dystrophy.

In some embodiments, the present disclosure provides a host cell comprising a nucleic acid encoding a biglycan-related therapeutic polypeptide.

In certain embodiments, the present disclosure provides a method of producing any of the biglycan-related polypeptides described herein, comprising: (a) providing a cell comprising a nucleic acid that encodes said polypeptide, and (b) culturing the cell under conditions that allow the production of said polypeptide. The method may further comprise a step of (c) purifying the polypeptide.

In certain aspects, the disclosure provides a method for detecting binding between MuSK and a biglycan, comprising: (a) affixing the biglycan to a solid support, (b) contacting the biglycan with a fusion protein comprising a MuSK ectodomain and a Fc domain, and (c) assaying binding of the biglycan to the fusion protein.

BRIEF DESCRIPTION OF THE FIGURES

FIG. 2 shows the sequence alignment between the Torpedo DAG-125 sequences (SEQ ID NOs: 1-3) and human biglycan (SEQ ID NOs: 4-6).

FIG. 9 shows bioactivity of NG and S5A-S10A biglycan in a cell culture bioassay. Upper panel: Primary chick myotubes were treated with 1 U of purified agrin and varying concentrations of either NG or S5A-S10A biglycan. The number of AChR clusters per myotube segment was then counted in triplicate cultures as described (Nastuk et al., 1991, PMID 1660286). The level of AChR clustering induced by agrin alone is indicated by the horizontal dotted line. Lower panel: the effects of PG, NG, and S5A-S10A on AChR clustering are shown.

FIG. 11a-c shows the functional efficacy of S5A-S10A rhBGN. Mdx mice were dosed with 10 mg/kg SA-rhBGN for 3 months at the intervals indicated. Eccentric contraction measurements were made on isolated muscle. Mdx mice were dosed with T2-rhBGN (10 mg/kg) or vehicle for 3 months at 7, 14, or 21 day intervals (Q7, Q14, Q21, respectively). Physiological properties of diaphragm muscle were measured by the ex vivo evaluation of force drop over 5 successive eccentric muscle contractions (ECC). (a) Force drop measurements after dosing at 7 day intervals. (b) Histograms of the force drop measured at the 5th ECC for each dose-frequency condition (n=5 or 6/group). (c) Animals dosed with T2-rhBGN every 7 days had a dramatic >50% improvement in muscle function at the 5th ECC ($p=0.007$). There was also a significant improvement at the 3rd and 4th ECCs ($p=0.01$, 0.005, respectively).

FIGS. 13 A and B show that the administration of biglycan to muscle tissue of a biglycan-null mouse restores collagen VI levels. A. Injected recombinant biglycan localizes to the surface of muscle cells. This image shows two fields of view showing immunolabeling of right quadriceps muscle from a biglycan null mouse with a biglycan antibody, four days post injection with 50 µg of purified recombinant biglycan proteoglycan. Light microscopy of the field showing deposits of India ink is shown in the upper panels. Injected purified recombinant biglycan proteoglycan was detected with the antibody 2A5. The lower panels show biglycan immunofluorescence in the same fields as the upper panels, and show that the injected biglycan persists in the muscle and localizes to the muscle fiber membranes. Similar results were observed in 6 animals. B. Injected recombinant biglycan upregulates collagen VI levels in vivo. This image shows two fields of view showing immunolabeling of right quadriceps muscle from a biglycan null mouse with an antibody to collagen VI shown four days after injection with 50 µg of purified recombinant biglycan proteoglycan. Light microscopy of the same field shows deposits of India ink (identifying the injection site). The lower panels show collagen immunofluorescence in the same fields as the upper panels, and show that injected purified recombinant biglycan proteoglycan upregulates collagen VI expression at the muscle fiber membranes. Similar results were observed in six animals.

FIG. 14 depicts the results of lectin blotting assays of recombinant NG, PG and SA forms of biglycan. Top panel, Ponceau staining and lectin blotting images. Bottom panel, summary of results.

FIG. 15 depicts the results of N-linked glycosylation analysis of the NG and SA forms of biglycan. The sequence "(R)MIEN@GSLSFLPTLR(E)", not including the two residues in parentheses, corresponds to residues 267-280 of SEQ ID NO: 9. The sequence "(K)LLQVVYLHSNN@ITK (V)", not including the two residues in parentheses, corresponds to residues 301-314 of SEQ ID NO: 9.

Figure 1:
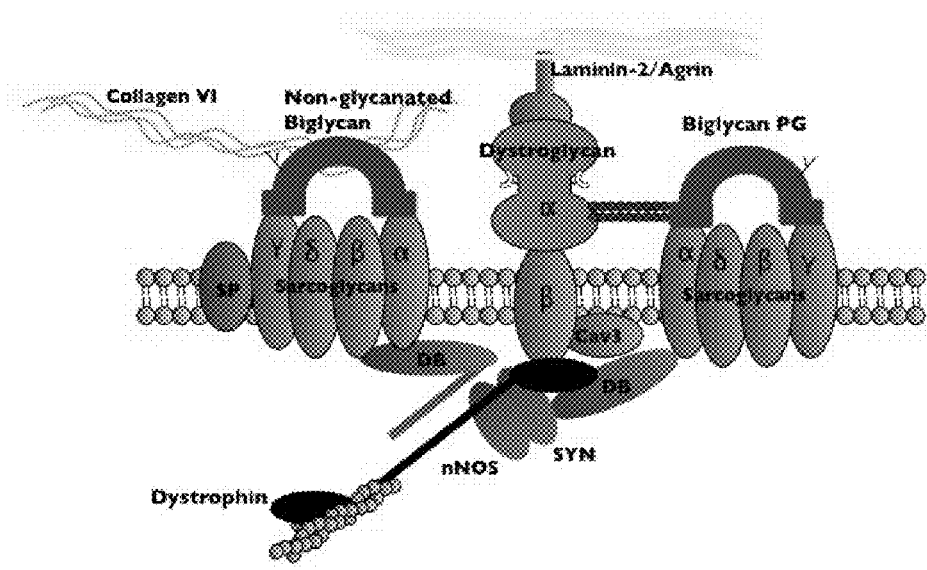
FIG. 1 is a diagram of the interaction between DAG-125 or biglycan with a DAPC.
Figure 3:
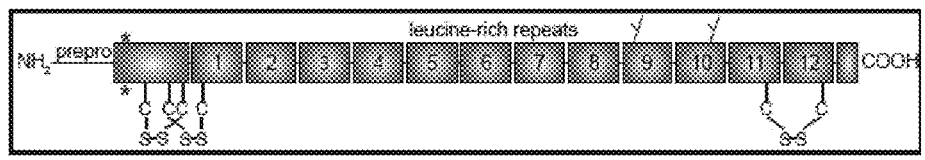
FIG. 3 is a diagram of the structure of biglycan. The prepro-region, which is absent in the mature biglycan corresponds to amino acids 1-37 of SEQ ID NO: 9; the N-terminal cysteine-rich region corresponds to amino acids 38-80 of SEQ ID NO: 9; the LRR region corresponds to about amino acids 81-314 of SEQ ID NO: 9; and the C-terminal cysteine-rich region corresponds to amino acids 315-368 of SEQ ID NO: 9. Circles represent attachment sites for chondroitin sulfate side chains. "S—S" denotes intrachain disulfide binding.

The term "glycoprotein" refers to a protein which contains one or more carbohydrate groups covalently attached to the polypeptide chain. Typically, a glycoprotein contains from 1% to 60% carbohydrate by weight in the form of numerous, relatively short, branched oligosaccharide chains of variable composition. In contrast to glycoproteins, proteoglycans are much larger (up to millions of daltons), and they contain 90% to 95% carbohydrate by weight in the form of many long, unbranched glycosaminoglycan chains.

The term "biglycan" refers to polypeptides having at least one biological activity of human biglycan or Torpedo DAG-125. Preferred biglycans include Torpedo DAG-125 (comprising SEQ ID NO: 1-3), human biglycan (SEQ ID NO: 9), as well as homologs and fragments thereof. Preferred homologs are proteins or peptides having at least about 70% identity, at least about 75% identity, at least about 80% identity, at least about 85% identity, at least about 90% identity, at least about 95% identity, and even more preferably, at least about 98 or 99% identity. Even more preferred homologs are those which have a certain percentage of homology (or identity) with human biglycan or Torpedo DAG-125 and have at least one biological activity of these molecules. The term biglycan is not limited to the full length biglycan, but includes also fragments (portions) having at least one activity of biglycan. Biglycan, as the term is used herein, refers to forms of the polypeptide both with and without the GAG side chains.

The term "wild-type human biglycan" refers to the protein described in Fischer et al. J. Biol. Chem. 264: 4571 (1989), having GenBank Accession No. J04599, and the amino acid sequence set forth in SEQ ID NO: 9. A cDNA sequence encoding the wild-type human biglycan protein is set forth in SEQ ID NO: 7, and the open reading frame thereof as SEQ ID NO: 8.

The term "biglycan core" refers to a biglycan that does not include GAG chains.

As described herein, the term "biglycan-related therapeutic" refers to a biglycan-like polypeptide in which the two amino acid residues corresponding to the two glycanated serine residues of a wildtype biglycan protein (e.g., Torpedo DAG-125 or a mammalian, preferably human, biglycan) are deleted or replaced by another amino acid (preferably glycine or an amino acid with an alkyl side chain, such as alanine) such that the polypeptide lacks glycosaminoglycan (GAG) side chains (i.e., because it lacks the wild-type glycanation sites). In addition, a biglycan-related therapeutic has one or more of the characteristics and biological activities of a wildtype biglycan. For example, a biglycan-related therapeutic may have one or more of the following characteristics: a molecular weight of between about 35 and about 55 kDa; an amino acid sequence at least 80%, 85%, 90%, 95%, or 99% identical to one or more of SEQ ID NOs: 1-6 or to residues 38-365 of SEQ ID NO: 9, 10, or 11; and one of more biological activities of biglycan, as listed infra, under the corresponding definition.

The term "biglycan-related therapeutic" further includes portions of the biglycan-like polypeptides described above and which have at least one biological activity of a wildtype biglycan. The term "biglycan-related therapeutic" also includes a peptidomimetic or derivative thereof, or a nucleic acid encoding a biglycan-like polypeptide.

A "biological activity of biglycan" is intended to refer to one or more of: the ability to maintain the integrity of a plasma membrane; the ability to stabilize DAPCs on plasma membranes; the ability to bind to one or more components of DAPCs; e.g., binding to α-dystroglycan (in the case of certain biglycans such as wild-type human biglycan), binding to a sarcoglycan component, such as α-sarcoglycan or γ-sarcoglycan; binding to MuSK; binding to collagen VI; stimulating the formation of neuromuscular junctions, such as by stimulating postsynaptic differentiation; potentiation of AChR aggregation, e.g., agrin-induced AChR aggregation; phosphorylation of DAPC components, e.g., sarcoglycans; stimulation MuSK phosphorylation or potentiating agrin-induced MuSK phosphorylation. In certain embodiments, the biglycan binds to MuSK, α-sarcoglycan, γ-sarcoglycan, and collagen VI, but does not bind to α-dystroglycan.

The term "biglycan nucleic acid" refers to a nucleic acid encoding a biglycan protein, e.g., a nucleic acid encoding a protein having SEQ ID NO: 9.

The term "abnormal" is used interchangeably herein with "aberrant" and refers to a molecule, or activity with differs from the wild type or normal molecule or activity.

The term "DAPC" refers to "dystrophin-associated protein complex", a membrane complex, set forth in FIG. 1, which comprises dystrophin, α- and β-dystroglycans, and the sarcoglycan transmembrane complex.

"Sarcoglycans" exit in different forms including α-, β-, γ-, delta-, and epsilon-sarcoglycans. Certain sarcoglycans are specific for certain tissues, e.g., α- and delta-sarcoglycans are skeletal muscle specific.

"Dystrophin-associated proteins" includes proteins or glycoproteins, such as α-dystroglycan, dystrobrevin, sarcospan and the syntrophins.

The term "AChR" refers to acetylcholine receptor.

The term "SLRP" refers to small leucine rich repeat proteoglycan.

The term "MuSK" used interchangeably herein with "muscle specific kinase," refers to a protein tyrosine kinase, that is expressed in normal and denervated muscle, as well as other tissues including heart, spleen, ovary or retina (See Valenzuela, D., et al., 1995, *Neuron* 15: 573-584). The tyrosine kinase has alternatively been referred to as "Dmk" for "denervated muscle kinase." Thus, the terms MuSK and Dmk may be used interchangeably. The protein appears to be related to the Trk family of tyrosine kinases, and is further described in U.S. Pat. No. 5,814,478.

The term "MuSK activating molecule" as used herein refers to a molecule which is capable of inducing phosphorylation of the MuSK receptor in the context of a differentiated muscle cell. One such activating molecule is agrin as described in the Examples set forth herein.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

A "myoblast" is a cell, that by fusion with other myoblasts, gives rise to myotubes that eventually develop into skeletal muscle fibres. The term is sometimes used for all the cells recognisable as immediate precursors of skeletal muscle fibres. Alternatively, the term is reserved for those post-mitotic cells capable of fusion, others being referred to as presumptive myoblasts.

"Myofibril" is a long cylindrical organelle of striated muscle, composed of regular arrays of thick and thin filaments, and constituting the contractile apparatus.

A "myotube" is an elongated multinucleate cells (three or more nuclei) that contain some peripherally located myofibrils. They are formed in vivo or in vitro by the fusion of myoblasts and eventually develop into mature muscle fibres that have peripherally located nuclei and most of their cytoplasm filled with myofibrils.

"Utrophin" (dystrophin associated protein) is an autosomal homologue of dystrophin (of size 395 kD) localized near the neuromuscular junction in adult muscle, though in the absence of dystrophin (i.e., in Duchenne muscular dystrophy), utrophin is also located on the cytoplasmic face of the sarcolemma.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene). Alternatively, a transgene can also be present in an episome. A transgene can include one or more transcriptional regulatory sequences and any other nucleic acid, (e.g., intron), that may be necessary for optimal expression of a selected coding sequence.

As used herein, the term "vector" refers to a nucleic acid molecule capable of transporting another nucleic acid to which it has been linked. One type of vector is an episome, i.e., a nucleic acid capable of extra-chromosomal replication. Appropriate vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "vector", unless otherwise specified, signifies "plasmid", as the plasmid is the most commonly used form of vector. However, the disclosure also provides such other forms of expression vectors which serve equivalent functions and which become known in the art subsequently hereto.

"Derived from" as that phrase is used herein indicates a peptide or nucleotide sequence selected from within a given sequence. A peptide or nucleotide sequence derived from a named sequence may contain a small number of modifications relative to the parent sequence, in most cases representing deletion, replacement or insertion of less than about 15%, preferably less than about 10%, and in many cases less than about 5%, of amino acid residues or base pairs present in the parent sequence. In the case of DNAs, one DNA molecule is also considered to be derived from another if the two are capable of selectively hybridizing to one another.

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

The term "modulate" refers to inhibiting or stimulating.

The terms "activating a postsynaptic membrane" refers to the stimulation of the transfer of a signal at neuromuscular junction, generally, from a nerve cell to a muscle cell. Activation usually includes the stimulation of aggregation of AChR on the cell membrane at the neuromuscular junction; and/or the phosphorylation of MuSK. Activation results in induction of postsynaptic differentiation.

The term "treating" with regard to a subject, refers to improving at least one symptom of the subject's disease or disorder. Treating can be curing the disease or condition or improving it, but reducing at least certain symptoms of it.

III. Biglycan-Related Therapeutic Polypeptides

One aspect of the present disclosure provides biglycan-related therapeutics for use in maintaining the integrity of plasma cell membranes, in particular, biglycan-related therapeutics which stabilize dystrophin associated protein complexes (DAPC) in these membranes, thereby preventing the disintegration of the membranes. The present disclosure also provides biglycan-related therapeutics which stimulate neuromuscular junction formation, such as by stimulating postsynaptic membrane differentiation, and more generally biglycan-related therapeutics which stimulate synapse formation.

In certain embodiments, biglycan-related therapeutics include a biglycan mutant polypeptide which comprises at least two amino acid residue substitutions at two serine residues (e.g., at residues 42 and 47 of SEQ ID NO: 9) such that the biglycan polypeptide does not comprise any glycosaminoglycan (GAG) side chain. For example, the biglycan mutant polypeptide may comprise the amino acid sequence of SEQ ID NO: 10, or a fragment thereof. SEQ ID NO: 10 is a consensus sequence, wherein residues 42 and 47 can each independently be absent or can be any amino acid except serine or threonine. In certain embodiments, residues 42 and 47 of SEQ ID NO: 10 are both present. In certain embodiments, the biglycan mutant polypeptide comprises the amino acid sequence of SEQ ID NO: 11, or a fragment thereof. SEQ ID NO: 11 is similar to SEQ ID NO: 9, but includes the mutations S42A and S47A.

The subject biglycan mutant polypeptides may be produced using any suitable technique. Numerous such techniques are well known in the art. For example, modification of the biglycan-encoding DNA sequence may be achieved by altering one or more nucleotides employing site-directed mutagenesis. In general, the technique of site specific mutagenesis is well known in the art as exemplified by publications (Carter et al., 1986, Biochem J., 237(1): 1-7; Sambrook, et al., 1989, Molecular Cloning: A Laboratory Manual, 2nd Ed., Cold Spring Harbor Laboratory, Cold Spring Harbor, N.Y.). As will be appreciated, the technique typically employs a phagemid vector which exists in both a single stranded and double stranded form. Alternatively, mutants may be generated by using the PCR™. Typical vectors useful in site-directed mutagenesis include vectors such as the M13 phage (Messing et al., 1981) or pUC 119. These vectors are readily commercially available and their use is generally well known to those skilled in the art. Alternatively, methods of site-directed mutagenesis employing double stranded plasmids or phagemids and the like are also well known in the art and may also be used.

In a particular embodiment, a biglycan-related therapeutic binds to one or more components of the DAPC. The biglycan therapeutic preferably binds to a sarcoglycan component, such as α-sarcoglycan. In an even more preferred embodiment, the biglycan therapeutic binds to a component of the sarcoglycan complex, e.g., selected from α-sarcoglycan, γ-sarcoglycan and δ-sarcoglycan. The component of the sarcoglycan to which the biglycan-related polypeptide binds is preferably α-sarcoglycan. Generally, biglycan-related therapeutic peptides contact one or more components of the DAPC, e.g., to thereby stabilize the complex and reduce destabilization of the plasma membrane resulting from an abnormal DAPC complex, such as those seen in muscular dystrophies.

In certain embodiments, the biglycan-related therapeutic binds to MuSK, α-sarcoglycan, γ-sarcoglycan, and collagen VI, but does not bind to α-dystroglycan. Even in embodiments where the biglycan is unable to bind α-dystroglycan, there are still mechanisms by which biglycan could influence α-dystroglycan indirectly. The following mechanisms should be considered non-binding theories: 1) biglycan may bind collagen VI and recruit other ligands for alpha-DG; this mechanism could occur in muscle or non-muscle tissues, 2) biglycan could bind to MuSK and thus indirectly recruit α-dystroglycan, and 3) since biglycan is known to dimerize, mutant biglycan incapable of binding α-dystroglycan might heterodimerize with the endogenous biglycan proteoglycan and thus recruit α-dystroglycan.

In other embodiments, biglycan-related therapeutics bind to the receptor tyrosine kinase MuSK. Such compounds can bind to MuSK and/or a component of the sarcoglycan complex, e.g., α-sarcoglycan. In preferred embodiments, a biglycan-related therapeutic activates MuSK and induces phosphorylation of α and/or γ-sarcoglycan.

The subject biglycan-related therapeutics preferably bind specifically to one or more of the above-cited molecules, i.e., they do not significantly or at a detectable level bind to other molecules to produce an undesirable effect in the cell. The biglycan-related therapeutics preferably bind with a dissociation constant of $10^{-6}$ or less, and even more preferably with a dissociation constant of $10^{-7}$, $10^{-8}$, $10^{-9}$, $10^{-10}$, $10^{-11}$, $10^{-12}$, or $10^{-13}$ M or less. The dissociation constant can be determined according to methods well known in the art.

Binding assays for determining the level of binding of a biglycan-related therapeutic to a component of the DAPC or to MuSK or for identifying members of, e.g., a library of compounds which bind to these molecules are known in the art and are also further described herein. Methods for preparing DAPC components or MuSK for use in such assays are also known. Such components can be isolated from tissue or, when they are proteins, can be prepared recombinantly or synthetically. Their nucleotide and amino acid sequences are publicly available, e.g., from GenBank, or from publications.

In other preferred embodiments, biglycan-related therapeutics have one or more biological activities of biglycan, in addition to, or instead of, being able to bind one or more components of the DAPC and/or MuSK. For example, a biglycan-related therapeutic can stimulate neuromuscular junction formation, in particular, postsynaptic membrane differentiation, including inducing aggregation of AChRs and/or stimulating agrin-induced tyrosine phosphorylation of MusK.

In certain embodiments, a biglycan-related therapeutic potentiates agrin-induced clustering of AChR in a biphasic manner, with a potentiation at low concentrations and a depotentiation at higher levels. Optionally, the biglycan-related therapeutic does not inhibit agrin-induced clustering of AChR at high concentrations.

In certain embodiments, a biglycan-related therapeutic decreases muscle damage in vivo.

The biglycan-related therapeutic can be a protein or derivative thereof, a peptidomimetic or derivative thereof, or a nucleic acid (e.g., a nucleic acid encoding a biglycan mutant polypeptide). Generally, the biglycan-related therapeutic has the required characteristics, e.g., binding to α-sarcoglycan and/or other DAPC components.

In certain embodiments, the biglycan-related therapeutic comprises one or more of the following amino acid sequence: IQAIEFEDL (SEQ ID NO: 1); LGLGFNEIR (SEQ ID NO: 2); and TSYHGISLFNNPVNYWDVL (SEQ ID NO: 3), or amino acid sequences related thereto, such as amino acid sequences from the mammalian ortholog of the Torpedo protein from which these amino acid sequences were obtained. The biglycan-related therapeutic preferably contain all three of these sequences or sequences related thereto. For example, the biglycan-related therapeutic can comprise one or more of the following amino acid sequences, which are part of human biglycan: IQAIELEDL (SEQ ID NO: 4); LGLGHNQIR (SEQ ID NO: 5); and AYYNGISLFNNPVPYWEVQ (SEQ ID NO: 6).

Although compositions including, and methods using, Torpedo DAG-125 are within the scope of the present disclosure, preferred compositions and methods are those relating to mammalian, including vertebrate, homologs of Torpedo DAG-125, referred to herein as orthologs of Torpedo DAG-125. Preferred orthologs of Torpedo DAG-125 are human, rodent, murine, canine, feline, ovine, and bovine orthologs. The mammalian ortholog of DAG-125 is biglycan.

A mammalian ortholog of Torpedo DAG-125 can be isolated by screening libraries with probes containing nucleotide sequences encoding one or more of SEQ ID NOs: 1-3. Numerous other methods are available for cloning the mammalian ortholog of Torpedo DAG-125. For example, antibodies to Torpedo DAG-125 can be produced and used to screen mammalian expression libraries. The identification of the cloned proteins as mammalian orthologs of Torpedo DAG-125 can be established by performing the same biological assays as those described in the Examples employing Torpedo DAG-125.

Thus, the polypeptides provided herein can also be members of the family of small leucine-rich proteoglycans (SLRP), also referred to as "nonaggreagating or small dermatan-sulfate proteoglycans" because of their inability to interact with hyaluronan, or because of their type of glycosaminoglycans, respectively. SLRPs are organized into three classes based on their protein and genomic organization. All SLRPs are characterized by a central domain containing leucine rich repeats (LRR) flanked at either side by small cysteine clusters. The SLRPs are described, e.g., in Iozzo et al. (1998) Ann. Rev. Biochem. 67:609, specifically incorporated herein by reference.

SLRP protein cores range from ~35-45 kD with one or two GAG chains attached at the extreme N-terminus. The general structure of the SLRP protein core consists of a tandem array of 6-10 leucine-rich repeats (LRR) flanked by domains with conserved, disulfide-bonded cysteines. Depending upon the extent of glycosylation and number of GAG chains, the native molecular weight ranges from ~100-250 kD. On the basis of their sequence homology, Iozzo, supra, has proposed that SLRPs be grouped into three classes consisting of: 1) biglycan and decorin; 2) fibromodulin, lumican, keratocan, PREPLP, and osteoadherin; and 3) epiphycan and osteoglycin. The most compelling feature of the SLRP protein core are the LRRs. Such repeats (24 aa each in the SLRPs) mediate protein-protein interactions in a wide variety of intracellular, transmembrane, and extracellular contexts (Kobe & Deisenhofer, (1994) Trends Biochem. Sci. 19: 415-21). The neurotrophin binding site on trkB, for example, is an LRR (Windisch et al., (1995) Biochemistry 34: 11256-63). The repeats are thought to have a general structure of an α-helix followed by beta-sheet in an anti-parallel array, although sequence analysis has suggested that this order might be reversed in the SLRPs (Hocking et al., (1998) Matrix Biol. 17: 1-19). It is likely that the conserved residues of each repeat dictate their secondary structure, while the intervening amino acids determine specificity of ligand binding.

SLRPs suitable for use in the methods herein include mutants of Class I SLRPs, such as biglycan and decorin. The partial amino acid sequences of DAG-125, the Torpedo proteoglycan which was shown to bind to α-dystroglycan (see, for example, U.S. Pat. No. 6,864,236) shows strong homology to human biglycan: a 78% identity was found in a total of 37 amino acid long sequence. Biglycan from rodent, pig and human are >95% identical. Decorin and biglycan from human are only 55% identical. Such homology is consistent with decorin and biglycan having both shared and unique functions. Thus, although Torpedo DAG-125 has amino acid sequence that more closely resemble that of human biglycan, based on the similarity of structure and function between biglycan and decorin, the latter proteoglycan and derivatives thereof may also be used to practice the methods herein.

Nucleotide and amino acid sequences of biglycan and decorin genes and proteins from various species are publically available, such as in GenBank. For example, human biglycan can be found under GenBank Accession No. J04599 (human hPGI encoding bone small proteoglycan I (biglycan), described in Fisher et al. (1989) J. Biol. Chem. 264: 4571; SEQ ID Nos: 7-9) and M65154; cow biglycan can be found under GenBank Accession No. L07953; rat biglycan can be found under GenBank Accession No. U17834, mouse biglycan can be found under GenBank Accession No. L20276 and X53928; ovis biglycan can be found under GenBank Accession No. AF034842; human decorin can be found at GenBank Accession No. M14219; rabbit decorin can be found at GenBank Accession No. 147020; chick decorin can be found at GenBank Accession No. P28675; Equus decorin can be found at GenBank Accession No. AF038; bovine decorin can be found at GenBank Accession No. P21793; ovis decorin can be found at GenBank Accession No. AF125041; and rat decorin can be found at GenBank Accession No. Q01129. Sequences of biglycan and decorin and other SLRPs can be found in GenBank.

Decorin and biglycan have one and two glycosaminoglycan (GAG) chains, respectively. Their composition is tissue specific and can be regulated at a number of levels (Hocking et al., (1998) Matrix Biol 17: 1-19). For example, the biglycan GAG from skin and cartilage is predominantly dermatan sulfate, while biglycan synthesized in bone is a chondroitin sulfate proteoglycan. Heparan sulfate side chains have not been reported. Both the protein core and the cell type contribute to the distinct glycosylation of these SLRPs.

In certain specific embodiments, biglycan-related therapeutics include fusion proteins. For example, a biglycan-like polypeptide or a portion thereof can be fused to an immunoglobulin portion. Alternatively, the fusion protein may be a combination between two or more portions of proteoglycans, e.g., a portion of a biglycan molecule fused to a portion of a decorin molecule.

In certain specific embodiments, biglycan-related therapeutics include portions and fragments of biglycan. A portion is typically at least 5, 10, 15, or 20 amino acids long. Preferred portions are sufficient for exerting a biological activity, such as interacting with a DAPC component. Portions can comprise or consist of one or more specific domain of a protein. Domains of biglycan and decorin include two cysteine-rich regions (included in the N- and C-terminal 40-50 amino acids of mature biglycan) and leucine-rich repeats (LRRs). The "LRR region" refers to the region of biglycan containing the repeats, and consists essentially of amino acids 81-314. Each individual repeat is referred to herein as an "LRR." LRRs are believed to mediate protein:protein interactions and may thus be sufficient for stabilizing DAPCs and postsynaptic membranes. Based at least on the observation that biglycan binds to MuSK, it is believed that the LRRs are involved in mediating the interaction of biglycan with MuSK and may be involved in mediating MuSK phosphorylation.

In a specific embodiment, the present disclosure provides a biglycan-related therapeutic which consists of a portion of biglycan that is capable of binding to a sarcoglycan. It has been shown that the α-sarcoglycan binding domain of human biglycan is located in the N-terminal domain of the mature biglycan protein, i.e., amino acids 38-80, and more specifically, amino acids 38-58 of SEQ ID NO: 9. It has also been shown that the C-terminal cysteine-rich domain mediates interaction with γ-sarcoglycan. Accordingly, a biglycan-related therapeutic may include portions (fragments) of biglycan consisting of the N-terminal or the C-terminal cysteine-rich domain, i.e., amino acids 38-80 and 315-368 of SEQ ID NO: 9. Combinations of certain domains of biglycan are also disclosed herein. For example, fragments of biglycan may consist of at least about 20, 30, 40, 50, 60, 70, 80, 90, 100, 150, or 200 amino acids. Short portions of biglycan-related therapeutics are termed "mini-biglycan-related therapeutics."

Wild-type human biglycan consists of 368 amino acids (SEQ ID NO: 9), of which amino acids 1-19 constitute a signal peptide (GenBank Accession No. NP_001702 and Fisher et al., supra). Thus wild-type human biglycan without a signal peptide consists of amino acids 20-368 of SEQ ID NO: 9. The mature biglycan protein consists of amino acids 38-368 of SEQ ID NO: 9, since amino acids 1-37, being a pre-propeptide, are cleaved during processing Amino acids 38-80 correspond to the N-terminal cysteine-rich region. About amino acids 81-314 corresponds to the leucine rich repeat region, containing 10 repeats of about 24 or 23 amino acids. The open reading frame in the cDNA encoding human biglycan corresponds to nucleotides 121-1227 of SEQ ID NO: 7 and is represented as SEQ ID NO: 8. The nucleotide sequence encoding a mature form of biglycan consists in nucleotides 232-1227 of SEQ ID NO: 7.

The biglycan-related therapeutic can be related to a mature form of the biglycan core, i.e., deprived of the signal peptide, or the full length biglycan with the signal peptide, provided that the two glycanated serines of the biglycan core are deleted or replaced by other amino acids as described herein.

Preferred biglycan-related therapeutics are encoded by nucleotide sequences which are at least about 70%, preferably at least about 80%, even more preferably at least about 85%, at least about 90%, at least about 95%, at least about 98%, or even more preferably at least about 99% identical to the nucleotide sequence of an SLRP, e.g., biglycan, or ortholog thereof, or portion thereof.

Preferred nucleic acids disclosed herein include those encoding a polypeptide comprising an amino acid sequence which is at least about 70%, preferably at least about 80%, even more preferably at least about 85%, at least about 90%, at least about 95%, at least about 98%, and even more preferably at least about 99% identical to the nucleotide sequence of an SLRP, e.g., biglycan (e.g., SEQ ID NO: 7 or 8 encoding human biglycan) or DAG-125 or ortholog thereof, portion thereof, provided that the two glycanated serines of the biglycan core are deleted or replaced by other amino acids as described herein. In one embodiment, the nucleic acid encodes a polypeptide containing one or more of SEQ ID NOs: 1-3 or SEQ ID NOs: 4-6 or 9.

Another aspect of the present disclosure provides a nucleic acid which hybridizes under stringent conditions to a nucleic acid encoding a biglycan-related therapeutic, e.g., having one or more of SEQ ID NOS: 1 to 6 or 9, or complement thereof. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In preferred embodiments, a nucleic acid encoding a biglycan-related polypeptide will bind to one of SEQ ID NOS 1 to 6 or complement thereof or nucleic acid encoding a SLRP under moderately stringent conditions, for example at about 2.0×SSC and about 40° C. In a particularly preferred embodiment, a nucleic acid according to the present disclosure will hybridize to a nucleotide sequence encoding one of SEQ ID NOS: 1 to 6 or 9, such as a nucleic acid having SEQ ID NO: 7 or 8, or a complement thereof under high stringency conditions.

Various methods for preparing the polypeptides and nucleic acids disclosed herein are well known in the art. For instance, the polypeptide or nucleic acid can be isolated from a tissue or the compound can be recombinantly or synthetically produced. The proteins isolated from tissue are preferably at least about 70%, preferably at least about 80%, at least about 85%, at least about 90%, at least about 95%, at least about 98% and most preferably, at least about 99% pure. Accordingly, preferred polypeptides may contain less than about 1%, and even more preferably less than about 0.1% of material from which the polypeptide was extracted.

The biglycan-related therapeutic polypeptide can also be produced recombinantly. Typically, a gene encoding the protein is inserted into a plasmid or vector, and the resulting construct is then transfected into appropriate cells, in which the protein is then expressed, and from which the protein is ultimately purified. Methods of producing and purifying biglycans are discussed in Mercado et al. ("Biglycan regulates the expression and sarcolemmal localization of dystrobrevin, syntrophin, and nNOS." Faseb J. 2006). Biglycan-related polypeptides may also be purified according to the method of Example 3. In some embodiments, the method of Example 3 is combined with further purification steps. These steps may utilize, for example, ion exchange resins.

Accordingly, the present disclosure further pertains to methods of producing the disclosed proteins. For example, a host cell transfected with an expression vector encoding a protein of interest can be cultured under appropriate conditions to allow expression of the protein to occur. The cells can be cultured in, for example, shake flasks or bioreactors. The protein may be secreted, by inclusion of a secretion signal sequence, and isolated from a mixture of cells and medium containing the protein. Alternatively, the protein may be retained cytoplasmically and the cells harvested, lysed and the protein isolated. A cell culture includes host cells, media and (typically) cell byproducts. Suitable media for cell culture are well known in the art. The proteins can be isolated from cell culture medium, host cells, or both. Techniques are known in the art for purifying proteins, including ion-exchange chromatography, gel filtration chromatography, ultrafiltration, electrophoresis, and immunoaffinity purification with antibodies specific for particular epitopes of the protein.

In some embodiments, the host cell is a mammalian cell, for instance a human cell or a rodent cell. Exemplary host cell lines include HEK (human embryonic kidney) 293 cells or CHO (Chinese hamster ovary) cells such as CHO—S cells.

Thus, a coding sequence for a biglycan-related therapeutic polypeptide can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance, suitable vectors for the expression of the instant fusion proteins include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIPS, YEP51, YEP52, pYES2, and YRP17 are cloning and expression vehicles useful in the introduction of genetic constructs into S. cerevisiae (see, for example, Broach et al., (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The protein can be produced either in eukaryotic cells, e.g., mammalian cells, yeast cells, insect cell (baculovirus system) or in prokaryotic cells.

Cells that can be used for producing a biglycan-related therapeutic can further be modified to increase the level and/or activity of an enzyme that catalyzes posttranslational modifications, e.g., glycosylations or sulfonations. For example, a cell can be transformed or cotransfected with an expression construct encoding a sulfotransferase, e.g., a chondroitin sulfotransferase, e.g., a chondroitin-6-sulfotransferase (C6ST; Fukuta et al. (1995) *J. Biol. Chem.* 270: 18575), or a nervous system involved sulfotransferase (NSIST), described in Nastuk et al. (1998) *J. Neuroscience* 18: 7167.

In some embodiments, a recombinant protein as described herein, such as biglycan or decorin, is produced as epitope-tagged, which facilitates co-immunoprecipitation and binding studies. One appropriate tag is the his tag. For example, a protein as described herein can be produced in a eukaryotic cell using the vaccinia virus/T7 bacteriophage expression system. A recombinant vaccinia virus, vBGN4 encoding the biglycan-related polypeptide, e.g., a mature biglycan protein, can be expressed as a polyhistidine fusion protein under control of the T7 phage promoter and expressed, e.g., in HT-1080 cells and UMR106 cells, as described in Hocking et al. (1996) *J Biol Chem* 271: 19571-7. There are also benefits to using an untagged protein, because an untagged protein is typically less likely to raise an immune response when administered to a subject.

Immortalized cell lines, e.g., muscle cell lines, such as biglycan negative cell lines, can be obtained as described in Jat et al., *PNAS* (1991) 88: 5096-100; Noble et al., (1992) *Brain Pathology* 2: 39-46. In one embodiment, a H-2K$^b$/tsA58 transgenic mouse is used. This mouse is a heterozygote harboring a thermolabile immortalizing gene (the tsA58 mutant of SV40 large T antigen) under the control of an interferon-inducible promoter (this mouse is available at Charles River). When cells containing this gene are cultured, they proliferate indefinitely at 33° C. in the presence of interferon. However, when the temperature is raised to 39° C. (at which temperature the tsA58 antigen is non-functional) and interferon is removed, the cells cease dividing. This method has been used for growing a wide variety of cell types, including astrocytes, osteoclasts, trabecular network, and colon epithelial cells (Chambers et al., (1993) *PNAS* 90: 5578-82; Groves et al., (1993) *Dev. Biol.* 159: 87-104; Whitehead et al., (1993) *PNAS* 90: 587-91; Noble et al., (1995) *Transgenic Res.* 4: 215-25; Tamm et al., (1999) *Invest. Ophtamol. Vis. Sci.* 40: 1392-403. This technique is well suited for the production of muscle cell lines. For example, in one study alone, 65 separate muscle cell lines were derived from animals ranging in age from neonates to four weeks (Morgan et al., (1994) *Dev. Biol.* 162 486-98). These lines were maintained for upwards of 80 generations. Remarkably, they not only formed myotubes when shifted to non-permissive conditions in culture, but also formed muscle when implanted into host mice. The H-2K$^b$/tsA58 transgenic method was also used by D. Glass and colleagues to produce a MuSK$^{-/-}$ muscle cell line (Sugiyama et al., (1997) *J. Cell Biol.* 139: 181-91).

To produce conditionally immortalized cell lines, mice having a specific mutation, e.g., a deficiency in biglycan or MuSK, can be crossed with heterozygote H-2K$^b$/tsA58 transgenic mice. The crosses are straightforward since only one copy of the gene is required for full activity. Muscle cells from neonatal animals can then be plated out and grown under permissive conditions (33° C. with interferon). Proliferating cells can then be cloned and samples from each line shifted to the non-permissive temperature and tested for their ability to form myotubes. Wild type; decorin$^{-/-}$; biglycan$^{-/o}$; and decorin$^{-/-}$ biglycan$^{-/o}$ cell lines are examples of cell lines which can be obtained using this technique.

The compounds described herein can also be peptidomimetics which can be prepared, e.g., based on the structure of the biglyan.

Certain methods for treating subjects with a biglycan-related therapeutic comprise the administration of the proteins described herein to the subject. However, the proteins can also be produced in a subject, by gene therapy techniques. Thus, e.g., a subject can receive an injection in a muscle (e.g., where the subject has a muscle dystrophy) of a vector encoding a biglycan-related therapeutic protein, such that the vector is capable of entering muscle cells and being expressed therein. Alternatively, the vector can be a viral vector, which is provided with the viral capside and the virus infects the cells, e.g., muscle cells and thereby deliver the vector. Methods and vectors for gene therapy are well known in the art. Illustrative methods are set forth below.

Preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant fusion proteins by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the -gal containing pBlueBac III).

In yet other embodiments, the subject expression constructs are derived by insertion of the subject gene into viral vectors including recombinant retroviruses, adenovirus, adeno-associated virus, and herpes simplex virus-1, or recombinant bacterial or eukaryotic plasmids. As described in greater detail below, such embodiments of the subject expression constructs are specifically contemplated for use in various in vivo and ex vivo gene therapy protocols.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a biglycan-related protein, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include SYMBOL 121 \f "Symbol"Crip, SYMBOL 121 \f "Symbol"Cre, SYMBOL 121 \f "Symbol"2 and SYMBOL 121 \f "Symbol"Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230: 1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, and can also be used to convert an ecotropic vector in to an amphotropic vector.

Another viral gene delivery system utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) BioTechniques 6:616; Rosenfeld et al., (1991) Science 252: 431-434; and Rosenfeld et al., (1992) Cell 68:143-155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482-6486), hepatocytes (Herz and Gerard, (1993) PNAS USA 90:2812-2816) and muscle cells (Quantin et al., (1992) PNAS USA 89:2581-2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored for use in the methods described herein are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted chimeric gene can be under control of, for example, the E1A promoter, the major late promoter (MLP) and associated leader sequences, the viral E3 promoter, or exogenously added promoter sequences.

Yet another viral vector system useful for delivery of the genes disclosed herein is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129). It is also one of the few viruses that may integrate its DNA into non-dividing cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol. Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

Other viral vector systems that may have application in gene therapy have been derived from herpes virus, vaccinia virus, and several RNA viruses. In particular, herpes virus vectors may provide a unique strategy for persistence of the recombinant gene in cells of the central nervous system and ocular tissue (Pepose et al., (1994) Invest Ophthalmol V is Sci 35:2662-2666).

In addition to viral transfer methods, such as those illustrated above, non-viral methods can also be employed to cause expression of a biglycan-related therapeutic protein in the tissue of an animal. Most nonviral methods of gene transfer rely on normal mechanisms used by mammalian cells for the uptake and intracellular transport of macromolecules. In certain embodiments, non-viral gene delivery systems rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding a protein of interest can be entrapped in liposomes bearing positive charges on their surface (e.g., lipofectins) and (optionally) which are tagged with antibodies against cell surface antigens of the target tissue (Mizuno et al., (1992) No Shinkei Geka 20:547-551; PCT publication WO91/06309; Japanese patent application 1047381; and European patent publication EP-A-43075). For example, lipofection of muscle, neural or cardiac cells can be carried out using liposomes tagged with monoclonal antibodies against specific tissue-associated antigens (Mizuno et al., (1992) Neurol. Med. Chir. 32:873-876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, any of the subject gene constructs can be used to transfect specific cells in vivo using a soluble polynucleotide carrier comprising an antibody conjugated to a polycation, e.g., poly-lysine (see U.S. Pat. No. 5,166,320). It will also be appreciated that effective delivery of the subject nucleic acid constructs via endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) Science 260-926; Wagner et al., (1992) PNAS USA 89:7934; and Christian et al., (1993) PNAS USA 90:2122).

Nucleic acids encoding biglycan-related proteins can also be administered to a subject as "naked" DNA, as described, e.g., in U.S. Pat. No. 5,679,647 and related patents by Carson et al., in WO 90/11092 and Felgner et al. (1990) Science 247: 1465.

In clinical settings, the gene delivery systems can be introduced into a patient by any of a number of methods. For instance, a pharmaceutical preparation of the gene delivery system can be introduced systemically, e.g., by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) PNAS USA 91: 3054-3057).

The gene encoding the biglycan-related therapeutic peptide can be under the control of a constitutive, or inducible promoter. These are well known in the art.

Methods for determining whether a compound has a biological activity of a wild-type biglycan protein are known in the art. A biological activity of a wild-type biglycan protein is intended to refer to one or more of: the ability to maintain the integrity of a plasma membrane; the ability to stabilize DAPCs on plasma membranes; the ability to bind to one or more components of DAPCs; e.g., binding to α-dystroglycan, binding to a sarcoglycan component, such as α-sarcoglycan; phosphorylation of α-sarcoglycan; binding to MuSK; binding to collagen VI stimulating the formation of neuromuscular junctions, such as by stimulating postsynaptic differentiation; stimulating AChR aggregation; stimulation of MuSK phosphorylation and potentiation of agrin-induced MuSK phosphorylation. Such methods can further be adapted for screening libraries of compounds for identifying compounds having one or more of the above-described activities.

Breakdown of cytoplasmic membranes, e.g., the presence of "leaky membranes" can be determined by assays which measure the release of creatine kinase or the absorption of Evans Blue dye, as described, e.g., in Tinsley et al. (1996) *Nature* 384: 349 and Straub et al. (1997) *J. Cell Biol.* 139: 375).

The biglycan-related therapeutics can also be tested in a variety of animal models, in particular the mdx mice, which are dystrophin negative (see, e.g., U.S. Pat. No. 7,612,038).

IV. Methods of Treatment

The present disclosure provides therapeutic and prophylactic methods of treatment of disorders including muscular, neuromuscular, neurological, and collagen VI-related disorders. Therapeutic methods are intended to eliminate or at least reduce at least one symptom of a disease or disorder, and preferably cure the disease or disorder. Prophylactic methods include those intended to prevent the appearance of a disease or disorder, i.e., a method which is intended to combat the appearance of the disease or disorder.

Wild-type biglycan was shown to bind to α-dystroglycan and to sarcoglycans, and thereby functions as a link between various components of DAPCs. Furthermore, biglycan levels were found to be high in muscle cells of mice lacking dystrophin (mdx mice, which are a model of muscular dystrophy). Since the absence of dystrophin in muscle cells is known to destabilize the cytoplasmic membrane, the upregulation of biglycan in dystrophin negative muscle cells may be a compensatory mechanism for the absence of dystrophin. Accordingly, in certain embodiments, the present disclosure provides for methods for preventing and treating diseases or disorders that are associated with plasma membrane instability or organization, in particular, an instability resulting from an abnormal DAPC on the plasma membrane. Since the DAPC is found on the membrane of muscle cells, diseases that can be treated using the methods herein include diseases of the muscle, such as muscular dystrophies and muscle atrophy.

In that regard, one promising path for treatment and potentially a cure for muscular dystrophy the activation of an endogenous compensatory mechanism based upon the regulated expression of utrophin. Utrophin is a homolog of dystrophin which shares numerous structural and functional properties with it. However, in both normal and in Duchenne's muscle utrophin is only expressed at a fraction of the muscle membrane: the neuromuscular junction and the myotendinous junction. The bulk of the membrane has no utrophin. However, in animal models it has been shown that forced expression of utrophin in muscle lacking dystrophin leads to restoration of the DAPC in the muscle membrane and to rescue of the dystrophic phenotype. Since the utrophin gene is normal in Duchenne patients, a method to activate its expression in muscle and/or to target it to the muscle membrane could serve to restore the DAPC to the membrane and thus promote the health of the muscle cells.

Several lines of evidence, many of them arising from observations made by the inventors, indicate that the small leucine-rich repeat proteoglycan biglycan could be used in a method for regulating utrophin expression and localization. It has been demonstrated that the protein agrin can cause an upregulation of utrophin expression and direct it to be localized to specific domains on the cell surface. The signaling receptor for agrin is the receptor tyrosine kinase MuSK. It has been observed that agrin can also induce the tyrosine phosphorylation of α- and γ-sarcoglycan in cultured myotubes. It was also observed that biglycan can also regulate the tyrosine phosphorylation of α- and γ-sarcoglycan. Moreover, the receptor tyrosine kinase MuSK is required for this biglycan-induced tyrosine phosphorylation of these proteins. Further, biglycan can bind to MuSK. These observations indicate that biglycan can act directly to organize the DAPC, including utrophin, on the muscle cell surface.

Thus the present application provides the treatment of these disorders with biglycan-related therapeutics which upregulate utrophin, activate MuSK and/or induce phosphorylation of sarcoglycans.

Merely to illustrate, biglycan-related therapeutics (e.g., polypeptides, peptides or peptidomimetics) can be delivered to patients with muscular dystrophy or other conditions where muscle atrophies to upregulate the endogenous utrophin gene expression and/or to promote the localization of utrophin to the muscle membrane. In such embodiments, the biglycan-related therapeutic polypeptide may be delivered in the form of a polypeptide in and of itself, or as part of a fusion protein, e.g., fused to a humanized antibody sequence or similar carrier entity. Biglycan-related therapeutic polypeptides can be delivered by nucleic acid-based methods including as plasmid DNA, in viral vectors, or other modalities where the nucleic acid sequences encoding the biglycan-related therapeutic polypeptides are introduced into patients. The delivery of a biglycan-related therapeutic can serve to heal the muscle fibers from within by directing the increased expression and regulated localization of utrophin to the muscle cell surface with concomitant restoration of the remainder of the dystrophin-associated protein complex.

Furthermore, since DAPCs are also found on other cell types, the present disclosure also provides methods for treating diseases associated with any abnormal DAPC. For example, DAPC are present in the brain, and since, in addition, agrin has been found in senile plaques in patients with Alzheimers's disease, neurological diseases can also be treated or prevented according to the methods described herein. A further indication that neurological disorders can be treated or prevented according to the methods described herein is based on the observation that patients with muscular dystrophy often also suffer from peripheral and central nervous system disorder. Accordingly, about one third of patients with Duchenne Muscular Dystrophy have a mental affliction, in particular, mental retardation. Thus, dystrophin, and hence, DAPCs, are believed to play a role in the nervous system.

Patients with Duchenne's Muscular Dystrophy also have diaphragm problems, indicating a role for dystrophin, and possibly DAPCs in diaphragms. Thus, compounds described herein would also find an application in disorders associated with diaphragm abnormalities.

It should be noted that diseases that can be treated or prevented include not only those in which biglycan is abnormal, but more generally any disease or condition that is associated with a defect that can be improved or cured by biglycan. In particular, diseases that are characterized by a defect or an abnormality in any component of the DAPC or component associated therewith, thereby resulting, e.g., in an unstable plasma membrane, can be treated or prevented according to the methods described herein, provided that the biglycan-related therapeutics can at least partially cure the defect resulting from the deficient component. In particular, diseases that can be treated according to the methods herein include any disease associated with an unstable DAPC, which can be rendered more stable by the presence of a biglycan-related therapeutic.

Furthermore, since biglycan was shown to bind to, and phosphorylates MuSK, a receptor which is known for mediating agrin-induced stimulation of neuromuscular junction formation, in particular postsynaptic membrane differentiation, to potentiate agrin-induced AChR aggregation, and to correct a defective agrin-induced AChR aggregation in myotubes of biglycan negative mice by its addition to the myotubes, the present disclosure also provides methods for preventing and treating diseases or disorders of neuromuscular junctions, such as neuromuscular disorders.

A. Exemplary Diseases and Disorders

Diseases or disorders that are characterized by a destabilization or improper organization of the plasma membrane of specific cell types include muscular dystrophies (MDs), a group of genetic degenerative myopathies characterized by weakness and muscle atrophy without nervous system involvement. The three main types are pseudohypertrophic (Duchenne, Becker), limb-girdle, and facioscapulohumeral. For example, muscular dystrophies and muscular atrophies are characterized by a breakdown of the muscle cell membrane, i.e., they are characterized by leaky membranes, which are believed to result from a mutation in a component of the DAPC, i.e., dystrophin. Mutations in the sarcoglycans are also known to result in muscular dystrophies and leaky membranes. Accordingly, the present disclosure provides methods for treating or preventing diseases associated with mutations in dystrophin and/or in sarcoglycans or other component of DAPCs, in particular muscular dystrophies.

Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20.

Another type of dystrophy that can be treated according to the methods herein includes congenital muscular dystrophy (CMD), a very disabling muscle disease of early clinical onset, is the most frequent cause of severe neonatal hypotonia. Its manifestations are noticed at birth or in the first months of life and consist of muscle hypotonia, often associated with delayed motor milestones, severe and early contractures and joint deformities. Serum creatine kinase is raised, up to 30 times the normal values, in the early stage of the disease, and then rapidly decreases. The histological changes in the muscle biopsies consist of large variation in the size of muscle fibers, a few necrotic and regenerating fibers, marked increase in endomysial collagen tissue, and no specific ultrastructural features. The diagnosis of CMD has been based on the clinical picture and the morphological changes in the muscle biopsy, but it cannot be made with certainty, as other muscle disorders may present with similar clinico-pathological features. Within the group of diseases classified as CMD, various forms have been individualized. The two more common forms are the occidental and the Japanese, the latter being associated with severe mental disturbances, and usually referred to as Fukuyama congenital muscular dystrophy (FCMD).

One form of congenital muscular dystrophy (CMD) has recently been characterized as being caused by mutations in the laminin alpha 2-chain gene Laminin is a protein that associates with DAPCs. Thus, the present disclosure also provides methods for treating diseases that are associated with abnormal molecules which normally associate with DAPCs.

Other muscular dystrophies include limb-girdle muscular dystrophy (LGMD), which represents a clinically and genetically heterogeneous class of disorders. These dystrophies are inherited as either autosomal dominant or recessive traits. An autosomal dominant form, LGMD1A, was mapped to 5q31-q33 (Speer, M. C. et al., Am. J. Hum. Genet. 50:1211, 1992; Yamaoka, L. Y. et al., Neuromusc. Disord. 4:471, 1994), while six genes involved in the autosomal recessive forms were mapped to 15q15.1 (LGMD2A) (Beckmann, J. S. et al., C. R. Acad. Sci. Paris 312:141, 1991), 2p16-p13 (LGMD2B) (Bashir, R. et al., Hum. Mol. Genet. 3:455, 1994), 13q12 (LGMD2C) (Ben Othmane, K. et al., Nature Genet. 2:315, 1992; Azibi, K. et al., Hum. Mol. Genet. 2:1423, 1993), 17q12-q21.33 (LGMD2D) (Roberds, S. L. et al., Cell 78:625, 1994; McNally, E. M., et. al., Proc. Nat. Acad. Sci. U.S.A. 91:9690, 1994), 4q12 (LG1MD2E) (Lim, L. E., et. al., Nat. Genet. 11:257, 1994; Bonnemann, C. G. et al. Nat. Genet. 11:266, 1995), and most recently to 5q33-q34 (LGMD2F) (Passos-Bueno, M. R., et. al., Hum. Mol. Genet. 5:815, 1996). Patients with LGMD2C, 2D and 2E have a deficiency of components of the sarcoglycan complex resulting from mutations in the genes encoding gamma-, alpha-, and beta-sarcoglycan, respectively. The gene responsible for LGMD2A has been identified as the muscle-specific calpain, whereas the genes responsible for LGMD1A, 2B and 2F are still unknown.

Yet other types of muscular dystrophies that can be treated according to the methods described herein include Welander distal myopathy (WDM), which is an autosomal dominant myopathy with late-adult onset characterized by slow progression of distal muscle weakness. The disorder is considered a model disease for hereditary distal myopathies. The disease is linked to chromosome 2p13. Another muscular dystrophy is Miyoshi myopathya, which is a distal muscular dystrophy that is caused by mutations in the recently cloned gene dysferlin, gene symbol DYSF (Weiler et al. (1999) Hum Mol Genet 8: 871-7). Yet other dystrophies include Hereditary Distal Myopathy, Benign Congenital Hypotonia, Central Core disease, Nemaline Myopathy, and Myotubular (centronuclear) myopathy.

Other diseases that can be treated or prevented according to the methods described herein include those characterized by tissue atrophy, e.g., muscle atrophy, other than muscle atrophy resulting from muscular dystrophies, provided that the atrophy is stopped or slowed down upon treatment with a biglycan-related therapeutic. Furthermore, the present disclosure also provides methods for reversing tissue atrophies, e.g., muscle atrophies. This can be achieved, e.g., by providing to the atrophied tissue a biglycan-related therapeutic.

Muscle atrophies can result from denervation (loss of contact by the muscle with its nerve) due to nerve trauma; degenerative, metabolic or inflammatory neuropathy (e.g., GuillianBarre syndrome), peripheral neuropathy, or damage to nerves caused by environmental toxins or drugs. In another embodiment, the muscle atrophy results from denervation due to a motor neuronopathy. Such motor neuronopathies include, but are not limited to: adult motor neuron disease, including Amyotrophic Lateral Sclerosis (ALS or Lou Gehrig's disease); infantile and juvenile spinal muscular atrophies, and autoimmune motor neuropathy with multifocal conduction block. In another embodiment, the muscle atrophy results from chronic disuse. Such disuse atrophy may stem from conditions including, but not limited to: paralysis due to stroke, spinal cord injury; skeletal immobilization due to trauma (such as fracture, sprain or dislocation) or prolonged bed rest. In yet another embodiment, the muscle atrophy results from metabolic stress or nutritional insufficiency, including, but not limited to, the cachexia of cancer and other chronic illnesses, fasting or rhabdomyolysis, endocrine disorders such as, but not limited to, disorders of the thyroid gland and diabetes.

Since muscle tissue atrophy and necrosis are often accompanied by fibrosis of the affected tissue, the reversal or the inhibition of atrophy or necrosis can also result in an inhibition or reversal of fibrosis.

In addition, the biglycan-related therapeutics may be of use in the treatment of acquired (toxic or inflammatory) myopathies. Myopathies which occur as a consequence of an inflammatory disease of muscle, include, but not limited to polymyositis and dermatomyositis. Toxic myopathies may be due to agents, including, but are not limited to amiodarone, chloroquine, clofibrate, colchicine, doxorubicin, ethanol, hydroxychloroquine, organophosphates, perihexyline, and vincristine.

Neuromuscular dystrophies include myotonic dystrophy. Myotonic dystrophy (DM; or Steinert's disease) is an autosomal dominant neuromuscular disease which is the most common form of muscular dystrophy affecting adults. The clinical picture in DM is well established but exceptionally variable (Harper, P. S., Myotonic Dystrophy, 2nd ed., W. B. Saunders Co., London, 1989). Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy (Harper, P. S., Myotonic Dystrophy, 2nd ed., W. B. Saunders Co., London, 1989). The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form, which occurs congenitally, is associated with generalized muscular hypoplasia, mental retardation, and high neonatal mortality. This disease and the gene affected is further described in U.S. Pat. No. 5,955,265.

Another neuromuscular disease is spinal muscular atrophy ("SMA"), which is the second most common neuromuscular disease in children after Duchenne muscular dystrophy. SMA refers to a debilitating neuromuscular disorder which primarily affects infants and young children. This disorder is caused by degeneration of the lower motor neurons, also known as the anterior horn cells of the spinal cord. Normal lower motor neurons stimulate muscles to contract. Neuronal degeneration reduces stimulation which causes muscle tissue to atrophy (see, e.g., U.S. Pat. No. 5,882,868).

The above-described muscular dystrophies and myopathies are skeletal muscle disorders. However, the present disclosure also pertains to disorders of smooth muscles, e.g., cardiac myopathies, including hypertrophic cardiomyopathy, dilated cardiomyopathy and restrictive cardiomyopathy. At least certain smooth muscles, e.g., cardiac muscle, are rich in sarcoglycans. Mutations in sarcoglycans can result in sarcolemmal instability at the myocardial level (see, e.g., Melacini (1999) *Muscle Nerve* 22: 473). For example, animal models in which a sarcoglycan is mutated show cardiac creatine kinase elevation. In particular, it has been shown that delta-sarcoglycan (Sgcd) null mice develop cardiomyopathy with focal areas of necrosis as the histological hallmark in cardiac and skeletal muscle. The animals also showed an absence of the sarcoglycan-sarcospan (SG-SSPN) complex in skeletal and cardiac membranes. Loss of vascular smooth muscle SG-SSPN complex was associated with irregularities of the coronary vasculature. Thus, disruption of the SG-SSPN complex in vascular smooth muscle perturbs vascular function, which initiates cardiomyopathy and exacerbates muscular dystrophy (Coral-Vazquez et al. (1999) *Cell* 98: 465).

Similarly to delta-sarcoglycan negative mice, mice lacking γ-sarcoglycan showed pronounced dystrophic muscle changes in early life (Hack et al. (1998) *J Cell Biol* 142: 1279). By 20 wk of age, these mice developed cardiomyopathy and died prematurely. Furthermore, apoptotic myonuclei were abundant in skeletal muscle lacking γ-sarcoglycan, suggesting that programmed cell death contributes to myofiber degeneration. Vital staining with Evans blue dye revealed that muscle lacking γ-sarcoglycan developed membrane disruptions like those seen in dystrophin-deficient muscle. It was also shown that the loss of γ-sarcoglycan produced secondary reduction of beta- and delta-sarcoglycan with partial retention of α- and epsilon-sarcoglycan, indicating that beta-, γ-, and delta-sarcoglycan function as a unit. Since the other components of the cytoplasmic membrane complex were functional, the complex could be stabilized by the presence of a biglycan-related therapeutic.

In addition to animal models, certain cardiomyopathies in humans have been linked to mutations in dystrophin, dystroglycans or sarcoglycans. For example, dystrophin has been identified as the gene responsible for X-linked dilated cardiomyopathy (Towbin J. A. (1998) *Curr Opin Cell Biol* 10: 131, and references therein). In this case, the dystrophin gene contained a 5'-mutation which results in cardiomyopathy without clinically-apparent skeletal myopathy (Bies et al. (1997) *J Mol Cell Cardiol* 29: 3175.

Furthermore, cardiomyopathy was also found in subjects having Duchenne's Muscular Dystrophy (associated with a mutated dystrophin), or other types of muscular dystrophies, such as Limb Girdle Muscular Dystrophy. For example, dilated cardiomyopathy was present in one autosomal dominant case and in three advanced autosomal recessive or sporadic patients, of whom two were found to have alpha sarcoglycan deficiency. Two of these three patients and three other cases showed ECG abnormalities known to be characteristic of the dystrophinopathies. A strong association between the absence of alpha sarcoglycan and the presence of dilated cardiomyopathy was found. In six autosomal dominant cases there were atrioventricular (AV) conduction disturbances, increasing in severity with age and in concomitant presence of muscle weakness. Pacemaker implantation was necessary in certain of these patients (see van der Kooi (1998) *Heart* 79: 73).

Biglycan-related therapeutics can also be used to treat or prevent cardiomyopathy, e.g., dilated cardiomyopathy, of viral origin, e.g., resulting from an enterovirus infection, e.g., a Coxsackievirus B3. It has been shown that purified Coxsackievirus protease 2A cleaves dystrophin in vitro and during Coxsackievirus infection of cultured myocytes and in infected mouse hearts, leading to impaired dystrophin function (Badorff et al. (1999) *Nat Med* 5: 320. Cleavage of dystrophin results in disruption of the dystrophin-associated glycoproteins α-sarcoglycan and β-dystroglycan. Thus, cardiomyopathy could be prevented or reversed by administration of a biglycan-related therapeutic to a subject having been infected with a virus causing cardiomyopathy, e.g., by disruption of dystrophin or a protein associated therewith. Administration of the therapeutic could restabilize or reorganize the cytoplasmic membrane of affected cardiac cells.

Thus, biglycan-related therapeutics can also be used to prevent or to treat smooth muscle disorders, such as cardiac myopathies, and to stop atrophy and/or necrosis of cardiac smooth muscle tissue. The treatment can also be used to promote survival of myocytes.

Neurological disorders that can be treated according to the methods described herein include polymyositis, and neurogenic disorders. Another neurological disease that can be treated is Alzheimers' disease.

Other diseases that can be treated according to the methods herein include those in which a proteoglycan is present at abnormal levels, or has an abnormal activity, relative to that in normal subjects. For example, a disease or disorder could be caused by a lower level of biglycan, resulting in, e.g., unstable cytoplasmic membranes. Alternatively, a disease or disorder could result from an abnormally high level or activity of biglycan, resulting in, e.g., overstimulation of MuSK or over-aggregation of AChRs (see below).

Yet other diseases or disorders that may be treated with the methods herein include those that are associated with an abnormal interaction between a proteoglycan and another molecule (other than those of the DAPC or MuSK), e.g., a complement factor, such as C1q. For example, it has been shown that C1q interacts with biglycan (Hocking et al. (1996) *J. Biol. Chem.* 271: 19571). It is also known that binding of C1q to cell surfaces mediates a number of biological activities including enhancement of phagocytosis and stimulation of superoxide production. Thus, since biglycan binds to C1q, a biglycan-related therapeutic may be used to inhibit the binding of C1q to its receptor on cell surfaces to inhibit one or more of such biological activities. In addition, a biglycan-related therapeutic which inhibits the interaction between C1q or other complement component and a cell surface can also be used to inhibit complement mediated necrosis of the cells and tissues containing such cells.

Furthermore, this application provides methods for preventing or inhibiting infections of cells by microorganisms, e.g., viruses. For example, it has been shown that dystroglycan is a receptor via which certain microorganisms enter eukaryotic cells (*Science* (1998) 282: 2079). Thus, by administrating to a subject a compound which, directly or indirectly, causes the site on dystroglycan molecules to which the microorganism binds to be unavailable, entering of the microorganism into the cell can be inhibited. This method can be used, e.g., to prevent or inhibit Lassa Fever virus and lymphocytic choriomeningitis virus (LCMV) infection, as well as infection by other arenaviruses, including Oliveros, and Mobala. Soluble α-dystroglycan was shown to block both LCMV and LFV infection (*Science* (1998) 282: 2079).

In addition to cell cultures, e.g., established from patients having, e.g., a muscular dystrophy, various animal models can be used to select the most appropriate biglycan-related therapeutic for treating a disease. In particular, to identify a therapeutic for use in preventing or treating a muscular dystrophy or cardiomyophaty associated with a mutated or absent DAPC component or, mice having mutated versions of these proteins, or having null mutations in the genes encoding these proteins, can be used. For example, mice having a disrupted sarcoglycan, such as delta-sarcoglycan, can be used. Such mice are described, e.g., Coral-Vazquez et al. (1999) *Cell* 98: 465. Alternatively, mice deficient in dystrophin (mdx mice), or in α- or γ-sarcoglycans can be used. Such mice have been described herein and in the literature. Additional mice can be made according to known methods in the art. In an illustrative embodiment to identify therapeutics, different therapeutics are administered to delta-sarcoglycan null mice, and the effect of the therapeutics are evaluated by studying cardiac function. Another animal model that can be used for this purpose is the cardiomyopathic hamster that does not express delta-sarcoglycan due to a genomic deletion. This rat is an animal model for autosomal recessive cardiomyopathy, and is further described in Sakamoto et al. *FEBS Lett* 1999 (1999) 44: 124.

Biglycan therapeutics may also be used to treat collagen VI disorders, as discussed in U.S. Patent Application 2005-0043221. In Application 2005-0043221, it was shown that biglycan null mice exhibited a striking reduction in collagen VI levels, as determined by immunofluorescence. As shown in Example 2, administration of biglycan to a mouse with a collagen VI deficiency resulted in increased levels of collagen VI in muscle. Therefore, the biglycans described herein may also be used to elevate collagen VI levels, thereby treating collagen VI disorders.

In general, the collagen VI disorder is one in which the subject produces a low, non-zero level or activity of collagen VI. In some embodiments, the disorder is characterized by a mutation that reduces, but does not completely eliminate, collagen VI activity. In some embodiments, the disorder is characterized by a reduction in collagen VI stability. In certain embodiments, the disorder is characterized by low, non-zero levels of collagen VI protein. For example, a heterozygous mutation (e.g., a haploinsufficiency) may result in reduced levels of collagen VI. Administration of a biglycan therapeutic is expected to increase the level of collagen VI, thereby treating the collagen VI disorder.

Thus, specific collagen VI disorders that may be treated according to methods disclosed herein include the following. Bethlem's myopathy is caused, at least in part, by mutations in collagen VI genes. In some embodiments, Bethlem's myopathy is caused by a haploinsufficiency (Pepe G et al., "COL6A1 genomic deletions in Bethlem myopathy and Ullrich muscular dystrophy." Ann Neurol. 2006 January; 59(1):190-5; Baker et al. "Molecular consequences of dominant Bethlem myopathy collagen VI mutations" Ann Neurol. 2007 October; 62(4):390-405). Collagen VI function is also compromised in Ullrich Congenital Muscular Dystrophy and Sorsby's fundus dystrophy. Like Bethlem myopathy, UCMD patients can have a wild-type copy of collagen VI (Jimenez-Mallebrera et al., "A comparative analysis of collagen VI production in muscle, skin and fibroblasts from 14 Ullrich congenital muscular dystrophy patients with dominant and recessive COL6A mutations" Neuromuscul Disord. 2006 October; 16(9-10):571-82). In certain embodiments, a collagen VI-related disorder may be treated by administering a biglycan therapeutic as described herein.

V. Effective Dose and Administration of Therapeutic Compositions

The above-described diseases or disorders can be treated or ameliorated in a subject by administering to the subject a pharmaceutically efficient amount of a bigylcan-related therapeutic. Depending on whether the disease is caused by higher levels or activity or by lower levels or activity of biglycan, an agonist or an antagonist biglycan-related therapeutic is administered to a subject having the disease. Although a person of skill in the art will be able to predict which therapeutic to administer for treating any of the diseases herein, tests can be performed to determine the appropriate therapeutic to administer. Such tests can use, e.g., animal models of the disease. Alternatively, in cases where diseases are due to a mutation in, e.g., biglycan, in vitro tests can be undertaken to determine the effect of the mutation. This will allow the determination of what type of therapeutic should be administered to a subject having this type of mutation.

Another manner of administering a biglycan-related therapeutic to a subject is by preparing cells expressing and secreting the biglycan-related therapeutic protein of interest, inserting the cells into a matrix and administering this matrix to the subject at the desired location. Thus, cells engineered in accordance with this disclosure may also be encapsulated, e.g., using conventional biocompatible materials and methods, prior to implantation into the host organism or patient for the production of a therapeutic protein. See e.g., Hguyen et al, Tissue Implant Systems and Methods for Sustaining viable High Cell Densities within a Host, U.S. Pat. No. 5,314,471 (Baxter International, Inc.); Uludag and Sefton, 1993, J Biomed. Mater. Res. 27(10):1213-24 (HepG2 cells/hydroxyethyl methacrylate-methyl methacrylate membranes); Chang et al, 1993, Hum Gene Ther 4(4):433-40 (mouse Ltk− cells expressing hGH/immunoprotective permselective alginate microcapsules; Reddy et al, 1993, J Infect Dis 168(4):1082-3 (alginate); Tai and Sun, 1993, FASEB J 7(11):1061-9 (mouse fibroblasts expressing hGH/alginate-poly-L-lysine-alginate membrane); Ao et al, 1995, Transplantation Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122(1):37-47 (polymer-encapsulated PC12 cells); Sagen et al, 1993, Neurosci 13(6):2415-23 (bovine chromaffin cells encapsulated in semipermeable polymer membrane and implanted into rat spinal subarachnoid space); Aebischer et al, 1994, Exp Neurol 126(2):151-8 (polymer-encapsulated rat PC12 cells implanted into monkeys; see also Aebischer, WO 92/19595); Savelkoul et al, 1994, J Immunol Methods 170(2):185-96 (encapsulated hybridomas producing antibodies; encapsulated transfected cell lines expressing various cytokines); Winn et al, 1994, PNAS USA 91(6):2324-8 (engineered BHK cells expressing human nerve growth factor encapsulated in an immunoisolation polymeric device and transplanted into rats); Emerich et al, 1994, Prog Neuropsychopharmacol Biol Psychiatry 18(5): 935-46 (polymer-encapsulated PC12 cells implanted into rats); Kordower et al, 1994, PNAS USA 91(23):10898-902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments, the cells to be encapsulated may express one or more therapeutic proteins of the host species and/or from viral proteins or proteins from species other than the host species.

Alternatively, the biglycan-related therapeutic is a nucleic acid encoding the biglycan-related therapeutic protein. Thus, a subject in need thereof, may receive a dose of viral vector encoding the protein of interest, which may be specifically targeted to a specific tissue, e.g., a dystrophic tissue. The vector can be administered in naked form, or it can be administered as a viral particle (further described herein). For this purpose, various techniques have been developed for modification of target tissue and cells in vivo. A number of viral vectors have been developed, such as described above, which allow for transfection and, in some cases, integration of the virus into the host. See, for example, Dubensky et al. (1984) Proc. Natl. Acad. Sci. USA 81, 7529-7533; Kaneda et al., (1989) Science 243, 375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g., intravascularly or intramuscularly, inhalation, or other parenteral mode. Non-viral delivery methods such as administration of the DNA via complexes with liposomes or by injection, catheter or biolistics may also be used.

In yet another embodiment, cells are obtained from a subject, modified ex vivo, and introduced into the same or a different subject. Additional methods of administration of the therapeutic compounds are set forth below.

A. Toxicity

Toxicity and therapeutic efficacy of biglycan-related therapeutics can be determined by standard pharmaceutical procedures in cell cultures or experimental animals, e.g., for determining the $LD_{50}$ (the dose lethal to 50% of the population of model organisms) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. In particular, where the therapeutic is administered for potentiating AChR aggregation, it is desirable to establish the dose that will result in stimulation, if desired, or inhibition, if desired. Tests can then be continued in medical tests. The dosage of such compounds lies preferably within a range of circulating concentrations that include the $ED_{50}$ with little or no toxicity. The dosage may vary within this range depending upon the dosage form employed and the route of administration utilized. For any compound used in the methods herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

B. Pharmaceutical Compositions

Pharmaceutical compositions for use in accordance with the present disclosure may be formulated in conventional manner using one or more physiologically acceptable carriers or excipients. Thus, the therapeutics and their physiologically acceptable salts and solvates may be formulated for administration by, for example, injection, inhalation or insufflation (either through the mouth or the nose) or oral, buccal, parenteral or rectal administration.

For such therapy, the biglycan-related therapeutics can be formulated for a variety of loads of administration, including systemic and topical or localized administration. Techniques and formulations generally may be found in Remington's Pharmaceutical Sciences, Meade Publishing Co., Easton, Pa. For systemic administration, injection may be used, including intramuscular, intravenous, intraperitoneal, and subcutaneous. For injection, the biglycan-related therapeutics can be formulated in liquid solutions, for instance in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated. Methods of coating tablets are well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); nonaqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the biglycan-related therapeutics are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the biglycan-related therapeutics are formulated into ointments, salves, gels, or creams as generally known in the art. A wash solution can be used locally to treat an injury or inflammation to accelerate healing.

In clinical settings, a gene delivery system for the therapeutic gene encoding a proteoglycan as described herein can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) PNAS 91: 3054-3057). A gene encoding a biglycan-related protein can be delivered in a gene therapy construct by electroporation using techniques described, for example, by Dev et al. ((1994) Cancer Treat Rev 20:105-115).

A mode of delivering DNA to muscle cells include using recombinant adeno-associated virus vectors, such as those described in U.S. Pat. No. 5,858,351. Alternatively, genes have been delivered to muscle by direct injection of plasmid DNA, such as described by Wolff et al. (1990) Science 247:1465-1468; Acsadi et al. (1991) Nature 352:815-818; Barr and Leiden (1991) Science 254:1507-1509. However, this mode of administration generally results in sustained but generally low levels of expression. Low but sustained expression levels are expected to be effective for practicing the methods herein.

The pharmaceutical preparation of the gene therapy construct or polypeptide can consist essentially of the gene delivery system or polypeptide in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

VI. Additional Exemplary Uses for the Biglycan-Related Therapeutics

The biglycan-related therapeutics can also be used as a supplement to a cell or tissue culture (e.g., system for growing organs). Any cell type may benefit from these supplements. The amount of compound to be added to the cultures can be determined in small scale experiments, by, e.g., incubating the cells or organs with increasing amounts of a specific biglycan-related therapeutic. Preferred cells include eukaryotic cells, e.g., muscle cells or neuronal cells.

Other preferred tissues include atrophic tissue. Thus, such tissue can be incubated in vitro with an effective amount of a biglycan-related therapeutic to reverse tissue atrophy. In one embodiment, atrophic tissue is obtained from as subject, the tissue is cultured ex vivo with a biglycan-related therapeutic in an amount and for a time sufficient to reverse the tissue atrophy, and the tissue can then be readminstered to the same or a different subject.

Alternatively, the biglycan-related therapeutics can be added to in vitro cultures of cells or tissue obtained from a subject having a muscular dystrophy, or other disease that can be treated with a biglycan-related therapeutic, to improve their growth or survival in vitro. The ability to maintain cells, such as brain cells or muscle cells from subjects having a muscular dystrophy or other disease, is useful, for, e.g., developing therapeutics for treating the disease.

VII. Protein Binding Assays

In some embodiments, the present disclosure provides methods of detecting binding between biglycan and MuSK. One such assay is described in Example 5 below. The biglycan can be in solution or affixed to a solid support such as a multiwell plate or a column. In some embodiments, peptide binding is determined by ELISA, co-immunoprecipitation, gel shift, or mass spectrometry. In some embodiments, the method further comprises comparing the binding to that of a positive control sample. In some embodiments, peptide binding indicates that the biglycan peptide is active.

The biglycan can be wild-type, such as the endogenous human or mouse biglycan sequence. In some embodiments, the biglycan peptide carries a mutation relative to the wild-type human biglycan sequence (SEQ ID NO: 9). In some embodiments, the biglycan peptide is SEQ ID NO: 11.

The MuSK ectodomain polypeptide comprises the MuSK ectodomain or a portion thereof and optionally other MuSK sequences or exogenous sequences, but does not comprise full-length MuSK. In some embodiments, the MuSK ectodomain peptide comprises an Fc domain.

In some aspects, the application provides a method for identifying an agent that modulates the interaction between MuSK and biglycan, comprising contacting biglycan with a MuSK protein comprising a MuSK ectodomain or a portion thereof sufficient for binding to biglycan and a test compound in conditions under which biglycan and the MuSK protein interact in the absence of the test compound, wherein a difference in the level of binding between the biglycan and MuSK protein in the presence of the test compound relative to the absence of the test compound indicates that the test compound is an agent that modulates the interaction between biglycan and MuSK.

VIII. Examples

The present invention is further illustrated by the following examples which should not be construed as limiting in any way. The contents of all cited references (including literature references, issued patents, published patent applications) as cited throughout this application are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Example 1: Preparation and Characterization of Different Forms of Biglycan

Biglycan is an extracellular matrix protein that is expressed as both a proteoglycan (PG) and a non-glycanated (NG) form. The proteoglycan form of biglycan contains either one or two glycosaminoglycan side chains that can be added at either serine 5 or serine 10 (numbering is based upon the sequence of the mature polypeptide).

We used recombinant DNA technology to create a mutant form of biglycan where the two serines that can be the site of GAG addition are mutated to alanines. This mutant is termed "S5A-S10A" or simply "SA". We also made a wild type construct. All were 6-HIS tagged and were based upon the human biglycan sequence. The prefix "His" is used to denote the presence of this tag.

Figure 4:
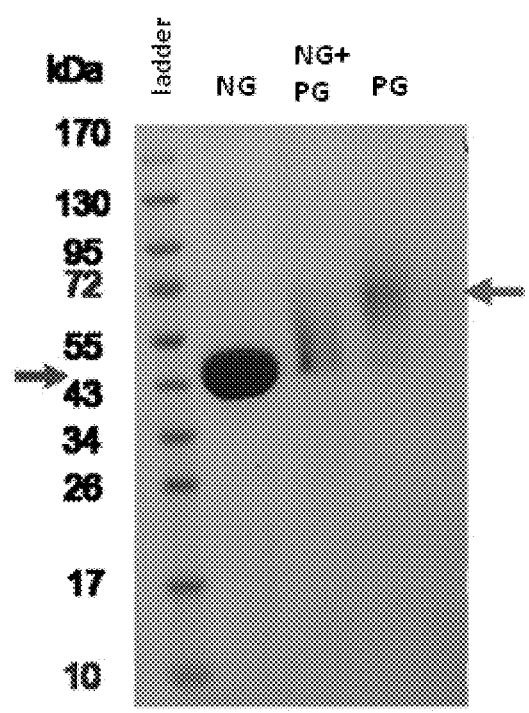
FIG. 4 shows the non-glycanated form (NG) and the proteoglycan form (PG) of biglycan. Final material was analyzed by SDS-PAGE followed by Coomassie Staining. Molecular weights of the ladder are indicated to the left of the gel. The arrow to the left of the gel indicates the non-glycanated form (NG) of biglycan and the light arrow to the right of the gel indicates the proteoglycan form (PG) of biglycan.
Figure 5:
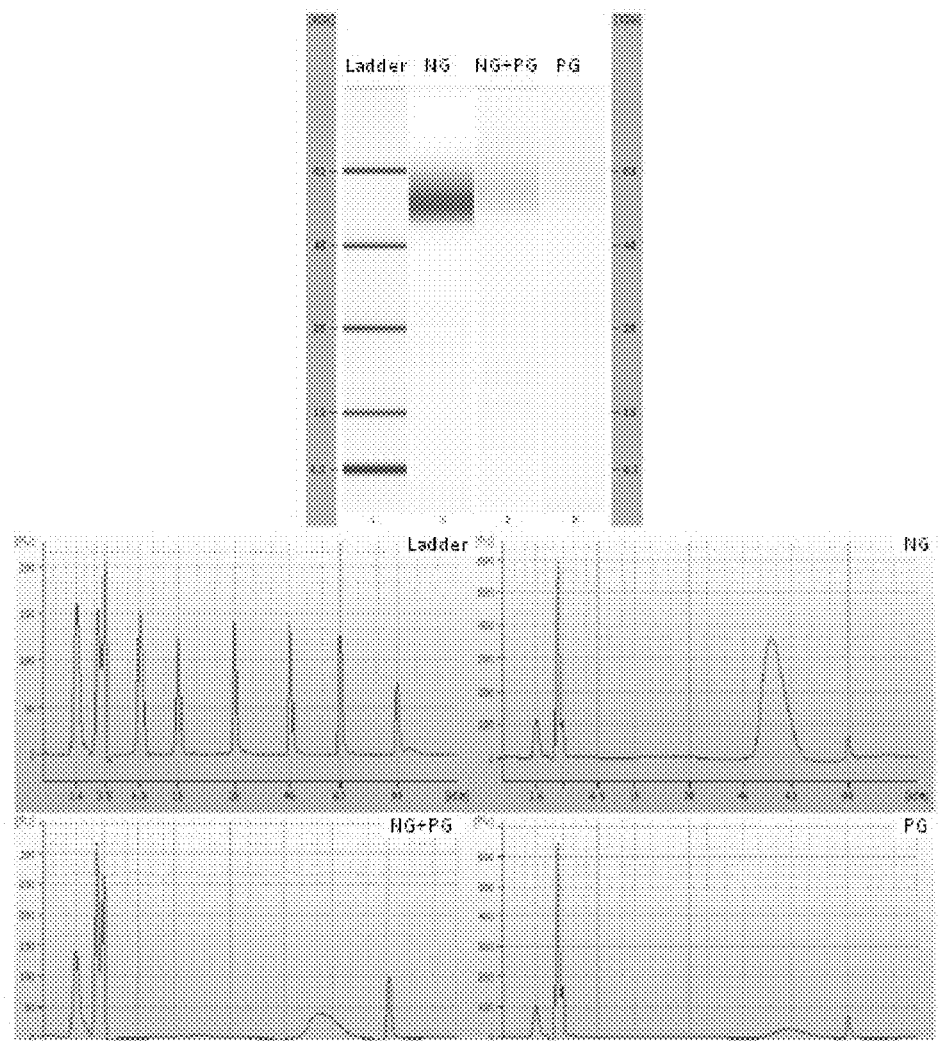
FIG. 5 shows analysis of the NG form and the PG form of biglycan. Final material was analyzed by Agilent Bioanalyzer 2100 Protein 80 chip assay. 2 µg total protein loaded per well. Top panel shows pseudo-gel image. Lower panels are electropherograms of the standards and each sample. Peaks below 4 kd and above 95 kd are system peaks used for chip calibration.

We produced and analyzed three forms of biglycan (PG, NG, S5A-S10A). All biglycan forms were made in HEK293 cells and purified by a combination of nickel and ion-exchange chromatography. These preparations were >90% pure as shown in FIGS. 4 and 5. Specifically, FIG. 4 shows the non-glycanated form (NG) and the proteoglycan form (PG) of biglycan as analyzed by SDS-PAGE followed by Coomassie Staining. FIG. 5 shows analysis of the NG form and the PG form of biglycan as analyzed by Agilent Bioanalyzer 2100 Protein 80 chip assay. For the NG form of biglycan, the apparent mass was 55.9 kd and the purity was 92.6%. For the mixture of NG and PG forms of biglycan, the apparent mass was 58.9 kd, and the purity was 74%. For the PG form of biglycan, the apparent mass was 60 kd, and the purity was not determined.

Figure 6:
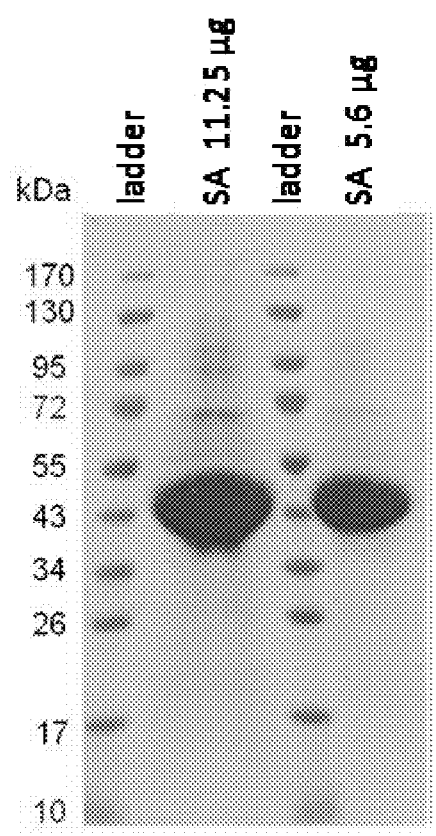
FIG. 6 shows analysis of S5A,S10A biglycan by SDS-PAGE. Final material was analyzed by SDS-PAGE followed by Coomassie staining. Molecular weights of the ladder are indicated to the left of the gel. The His-Biglycan (S5A, S10A) double mutant, designated SA, was loaded on the gel in two different amounts, indicated above each lane.
Figure 7:
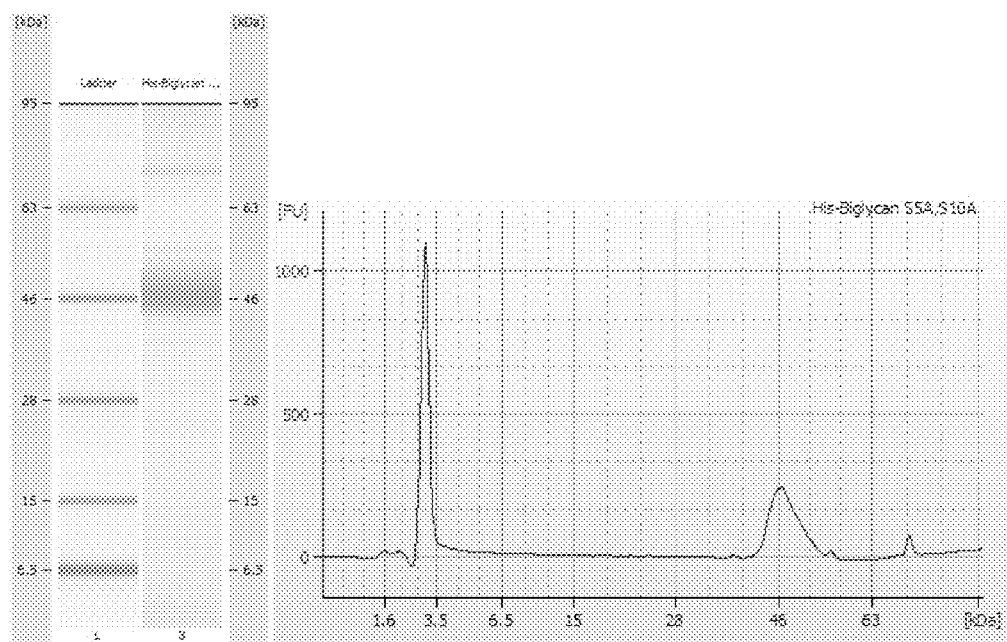
FIG. 7 shows final analysis of S5A,S10A biglycan by Agilent Bioanalyzer 2100. 2 µg of His-Biglycan (S5A, S10A) was loaded on a Protein 80 chip. Left panel is the pseudo-gel image. Right panel shows the electropherogram. Bands below 6 kd and above 95 kd are system peaks used for calibration.

The purity of the S5A-S10A preparation were also >90% as shown in FIGS. 6 and 7. Specifically, FIG. 6 shows analysis of S5A,S10A biglycan as analyzed by SDS-PAGE followed by Coomassie Staining. FIG. 7 shows finally analysis of S5A,S10A biglycan by Agilent Bioanalyzer 2100. The apparent mass was 46.3 kd and the purity was 93.2%.

Figure 8:
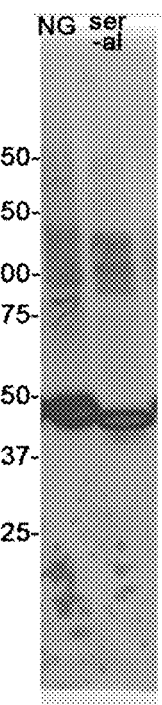
FIG. 8 shows western blot analysis of recombinant non-glycanated (NG) and S5A,S10A mutant biglycan. Samples were run on an SDS PAGE, transferred to a nitrocellulose membrane and probed with a biglycan antibody. The lane marked "ser-al" contains the S5A; S10A biglycan. The indicated amino acid positions are those of mature protein.

Western blot data shows that the S5A-S10A migrated faster on SDS gels than the NG, consistent with the presence of O-linked glycosylation on S5 and/or S10 (FIG. 8). FIG. 8 shows western blot analysis of recombinant non-glycanated (NG) and S5A,S10A mutant biglycan. Samples were run on an SDS PAGE, transferred to a nitrocellulose membrane and probed with a biglycan antibody. "ser-al" is double mutant of the both the GAG addition sites (S5A; S10A). Amino acid positions are for mature protein. Note that the mobility of the S5A; S10A mutant was faster than the (wild type) non-glycanated. These data indicate that one or both of the serines is modified in the non-glycanated. Note that the relative mobility of the NG sample is different in FIG. 6 due to gel systems use to generate this Figure as compared to that in FIGS. 4 and 5. All of the NG samples have the same mobility when separated on the same system.

Glycosyl analysis by gas chromatography of the total carbohydrates of the NG and the S5A-S10A revealed that there were major differences between them (Table 1). Notably, total glycosylation of S5A-S10A was 57% of that in NG. No iduronic or glucuronic acid was detected in NG, indicating that there was no GAG present in NG preparation. For comparison, both iduronic and glucuronic acid are highly enriched in PG proteoglycan (see Table 1 below).

Methods of determining glycosyl composition by GC-MS (Table 1) were carried out as follows. The samples (to provide ~125 µg based on undialyzed sample information) allocated for monosaccharide composition analysis were placed in screw-cap tubes, added with 10 µg inositol as internal standard, and lyophilized. Methyl glycosides then were prepared from the dried samples by methanolysis with 3 M HCl in methanol at 100° C. for 2 h followed by re-N-acetylation with pyridine and acetic anhydride in methanol (for detection of amino sugars). The preceding methanolysis and re-N-acetylation steps were repeated two times. The samples then were per-O-trimethylsilylated (TMS) with a Tri-Sil reagent (Thermo Scientific) at 80° C. for 0.5 h. These procedures were carried out as described previously in Merkle and Poppe (1994) *Methods Enzymol.* 230:1-15; York, et al. (1985) *Methods Enzymol.* 118:3-40. Analysis of the TMS methyl glycosides was performed on a Hewlett Packard Series II 5890 gas chromatograph equipped with a Supelco EC-1 fused silica capillary column (30 m×0.25 mm ID) and interfaced to a Hewlett Packard 5970 MSD.

GNA and MAA and strongly stained by SNA and DSA. These results indicate that the glycans on NG and SA protein have terminal mannose, Sialic acid linked (2-6) and (2-3) to Gal or GalNAc, and Galβ(1-4)GlcNAc or terminal GlcNAc, while PG protein glycans contains Sialic acid linked (2-3) to Gal, and Galβ(1-4)GlcNAc or terminal GlcNAc structures.

Lectin blotting was carried out using DIG glycan differentiation kit (Roche). Briefly, the sample and controls were blotted onto the nitrocellulose membrane (1 µg of the sample, positive and negative control. The membranes were immersed in a blocking solution (supplied by the kit) followed by incubation with Digoxigenin-labeled lectins at 1 µg/ml in TBS. The binding activity was visualized using 750 mU alkaline-phosphatase-conjugated sheep anti-Digoxigenin as secondary antibody and nitro blue tetrazolium/5-bromo-4-chloro-3-indolyl phosphate as color developing reagent. Carboxypeptidase Y (a, GNA positive), Transferrin (b, SNA positive), Fetuin (c, MAA positive) and Asialofetuin (d, PNA and DSA positive) were used as

TABLE 1

Glycosyl composition analysis of biglycan glycoforms by GC-MS. "Mutant" denotes S5A-S10A.

| Sample | Glycosyl residue | Mass (µg) | Mole % |
|---|---|---|---|
| Non-glycanated | Iduronic acid | nd | — |
| | Fucose (Fuc) | 0.21 | 17.1 |
| | Xylose (Xyl) | 0.10 | 8.7 |
| | Glucuronic Acid (GlcA) | nd | — |
| | Galacturonic acid (GalA) | nd | — |
| | Mannose (Man) | 0.46 | 34.8 |
| | Galactose (Gal) | 0.29 | 21.6 |
| | N-Acetyl Galactosamine (GalNAc) | nd | — |
| | N-Acetyl Glucosamine (GlcNAc) | 0.29 | 17.8 |
| | N-Acetyl Mannosamine (ManNAc) | nd | — |
| | Total | 1.34 | 100.0 |
| | Percent total carbohydrate by weight | 1.07 | |
| Proteoglycan | Iduronic acid | 5.28 | 12.5 |
| | Fucose (Fuc) | 0.86 | 1.9 |
| | Xylose (Xyl) | 0.50 | 1.2 |
| | Glucuronic Acid (GlcA) | 10.18 | 18.6 |
| | Galacturonic acid (GalA) | 0.30 | 0.5 |
| | Mannose (Man) | 0.17 | 0.3 |
| | Galactose (Gal) | 3.14 | 6.2 |
| | N-Acetyl Galactosamine (GalNAc) | 28.00 | 44.8 |
| | N-Acetyl Glucosamine (GlcNAc) | 7.92 | 12.7 |
| | N-Acetyl Mannosamine (ManNAc) | 0.89 | 1.4 |
| | Total | 57.23 | 100.0 |
| | Percent total carbohydrate by weight | 45.78 | |
| Mutant protein = | Iduronic acid | nd | — |
| | Fucose (Fuc) | 0.02 | 3.9 |
| | Xylose (Xyl) | 0.02 | 3.5 |
| | Glucuronic Acid (GlcA) | nd | — |
| | Galacturonic acid (GalA) | nd | — |
| | Mannose (Man) | 0.09 | 14.4 |
| | Galactose (Gal) | 0.02 | 2.6 |
| | N-Acetyl Galactosamine (GalNAc) | nd | — |
| | N-Acetyl Glucosamine (GlcNAc) | 0.61 | 75.5 |
| | N-Acetyl Mannosamine (ManNAc) | nd | — |
| | Total | 0.77 | 100.0 |
| | Percent total carbohydrate by weight | 0.61 | | nd = not detected.

The different forms of biglycan were further characterized by lectin blotting (FIG. 14). The recombinant bilgycan samples NG (non-glycanated), PG (proteoglycan), SA (mutant) and the controls BSA, Carboxypeptidase Y (a), Transferrin (b), and Asialofetuin (d) were stained by Ponceau S. Fetuin (c) was hardly stained by Ponceau S, perhaps because this glycoprotein is highly glycosylated and sialylated. PG was stained by MAA and DSA. SA was slightly stained by positive controls. Bovine serum albumin (BSA) was used as a negative control. Ponceau S staining was used for detection of protein on the membrane.

In addition, the position of N-linked glycosylation on different forms of biglycan was determined (FIG. 15). There are 2 potential N-glycosylation sites on SA protein; $Asn^{248}$ and $Asn^{288}$ are found within N-X-S/T consensus sequences for N-glycosylation. The SA mutant biglycan was digested with trypsin and the glycopeptides were deglycosylated with PNGase F in $H_2^{18}O$ converting the glycosylated asparagine residues into aspartic acid residues. A glycosylated peptide shows an increase of 3 Da mass compared to the corresponding non-glycosylated peptide. Glycosylation sites $Asn^{248}$ and $Asn^{288}$ of SA were shown to be glycosylated by LC-MS/MS in conjunction with a parent mass list monitoring method and database searching using the TurboSequest algorithm. The summary of N-linked glycosylation site peptides from SA is shown in FIG. 15. These results indicated that two potential N-linked glycosylation site of SA are fully glycosylated. It is worth noting that the numbering of amino acids in SA is different from that of NG. However, peptide sequence including N-glycosylation sites are identical between the two samples and the numbering in for the NG sample is consistent with that found in the UniProt database.

To perform the N-linked glycosylation analysis, fifty micrograms of the SA biglycan was reduced with 25 mM DTT for 1 h at 55° C. and carboxyamidomethylated with 90 mM iodoacetamide in the dark for 45 min. The dried dialyzed sample was resuspended in 50 mM ammonium bicarbonate ($NH_4HCO_3$) and digested with 2.5 µg of trypsin at 25° C. for 20 h. Following deactivation of trypsin at 100° C. for 5 min, the sample was then deglycosylated with 2 µg of PNGaseF in 36 µL of $^{18}O$ Water ($H_2^{18}O$) and 2 µL of 1 M $NH_4HCO_3$.

The labeled peptides were resuspended with 200 µL of mobile phase A (0.1% formic acid in water). The sample was then loaded onto a nanospray tapered capillary column/emitter (360×75×15 µm, PicoFrit, New Objective, Woburn, Mass.) self-packed with C18 reverse-phase resin (10.5 cm, Waters, Milford, Mass.) in a nitrogen pressure bomb apparatus for 10 min at 1,000 psi (~5 uL load) and then separated via a 160 min linear gradient of increasing mobile phase B at a flow rate of ~500 mL/min directly into the mass spectrometer.

LC-MS/MS analysis was performed on a LTQ Orbitrap Discoverer mass spectrometer (Thermo Scientific) equipped with a nanospray ion source. The resulting data were searched against the recombinant SA sequence using the TurboSequest algorithm (Proteome Discoverer 1.1, Thermo Scientific). The SEQUEST parameters were set to allow 30.0 ppm of precursor ion mass tolerance and 0.8 Da of fragment ion tolerance with monoisotopic mass. Tryptic peptides were allowed with up to two missed internal cleavage sites, and the differential modifications of 57.02146 Da, 15.9949 Da and 2.98826 Da were allowed for alkylated cysteine, oxidation of methionines and $^{18}O$-labeled aspartic acid, respectively.

For the NG sample, all of the above procedures were followed, except for the initial steps. Forty micrograms of NG was reduced with 25 mM DTT for 1 h at 55° C. and carboxyamidomethylated with 90 mM iodoacetamide in the dark for 45 min. The dried dialyzed sample was resuspended in 50 mM ammonium bicarbonate ($NH_4HCO_3$) and digested with 2 µg of trypsin at 25° C. for 20 h. Following deactivation of trypsin at 100° C. for 5 min, the sample was then deglycosylated with 2 µg of PNGaseF in 36 µL of $^{18}O$ Water ($H_2^{18}O$) and 2 µL of 1M $NH_4HCO_3$.

Together, these data indicate that the "non-glycanated" and SA mutant forms of biglycan do contain some carbohydrate moieties, but these differ from the proteoglycan form of biglycan.

Bioactivity comparison of NG and S5A-S10A showed distinct activities. S5A-S10A shows a biphasic response (potentiation and depotentiation), while NG shows a triphasic response (potentiation, depotentiation, and inhibition (FIG. 9). FIG. 9 (upper panel) shows bioactivity of NG and S5A-S10A biglycan in a cell culture bioassay. Primary chick myotubes were treated with 1 U of purified agrin and varying concentrations of either NG or S5A-S10A biglycan. The number of AChR clusters per myotube segment was then counted in triplicate cultures as described (Nastuk et al., 1991, PMID 1660286). The level of AChR clustering induced by agrin alone is indicated by the horizontal dotted line. Note that S5A-S10A shows potentiation at low concentrations (≤0.05 µg/ml) and depotentiation at all higher concentrations. In contrast, NG biglycan shows potentiation at ≤0.05 µg/ml, but then demonstrates depotentiation and inhibition at higher concentrations. Compared to SA and NG, PG shows a markedly different effect on AChR clustering (see lower panel).

Figure 10:
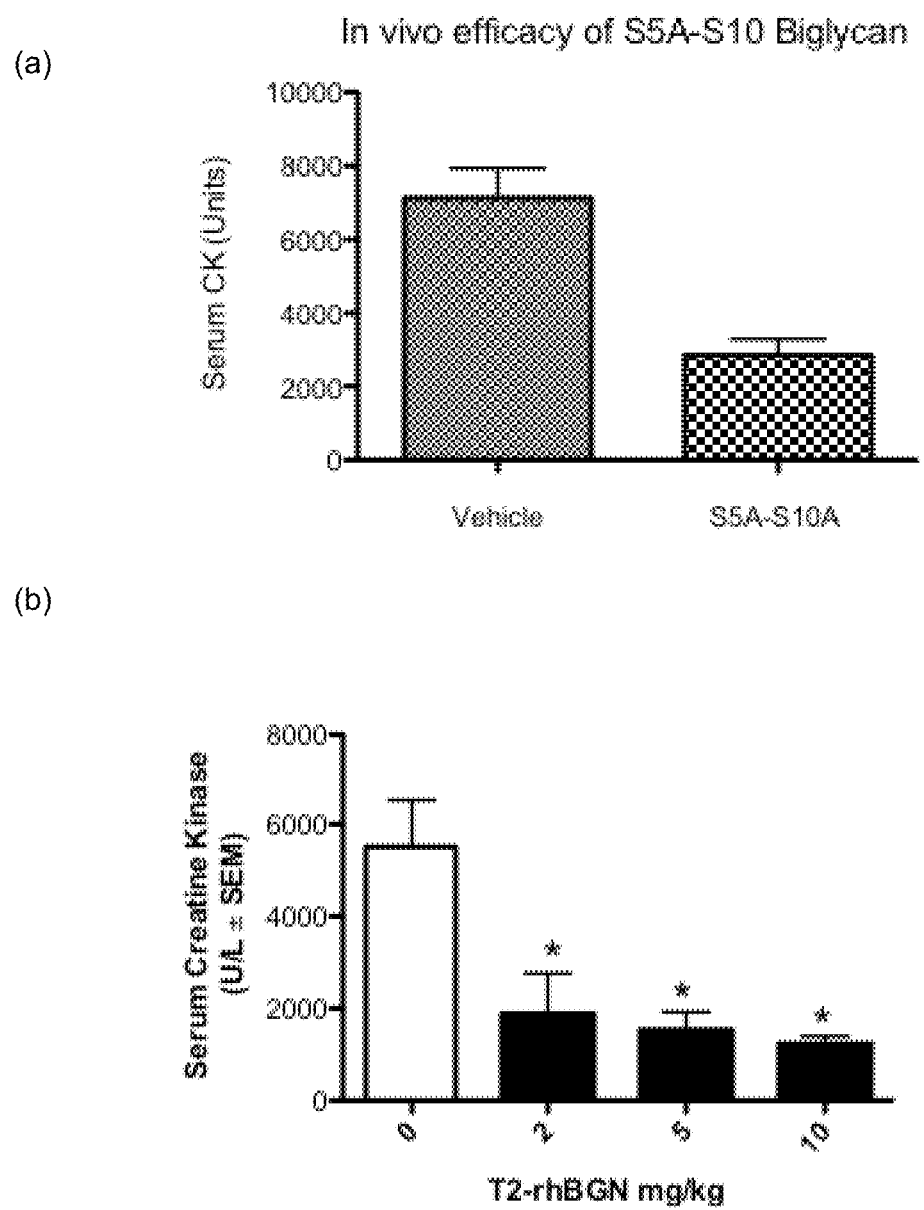
FIGS. 10a and b show that S5A-S10A biglycan decreases muscle damage in mdx mice. (a) P18 Mdx mice were injected weekly intraperitoneally for two weeks with either vehicle or S5A-S10A biglycan and the levels of serum Creatine Kinase (sCK) were measured. The levels of sCK were reduced over 2-fold in the biglycan-injected animals. ($p<0.01$; n=4). (b) Mdx mice were injected at P18 and P25 with the indicated amounts of his-tagged S5A-S10A recombinant human biglycan (T2-rhBGN). Serum was harvested at P32. (ANOVA $p=0.002$; *post-hoc pairwise comparison $p<0.05$.)

We found that S5A-S10A was active in vivo. Systemic injection of S5A-S10A to mdx mice decreased muscle cell damage as assessed by measurement of serum Creatine Kinase levels (FIG. 10). FIG. 10 shows that S5A-S10A biglycan decreases muscle damage in mdx mice. In FIG. 10a, P18 Mdx mice were injected weekly intraperitoneally for two weeks with either vehicle or S5A-S10A biglycan and the levels of serum Creatine Kinase (sCK) were measured. The levels of sCK were reduced over 2-fold in the biglycan-injected animals. (p<0.01; n=4). FIG. 10b shows that the reduction in sCK depends on the dose of S5A-S10A biglycan administered.

FIG. 11 shows the functional efficacy of S5A-S10A rhBGN. Mdx mice were dosed with 10 mg/kg SA-rhBGN by intraperitoneal injection for 3 months at the intervals indicated. Eccentric contraction measurements were made on isolated muscle. Muscle length was adjusted to achieve maximal twitch response and this length (Lo) was measured. Eccentric contraction force decrease was calculated for each tetanus of a standard ECC protocol of supramaximal stimulus 700 ms, total lengthening Lo/10; lengthening velocity 0.5 Lo/s. A dose-frequency response in improvement of muscle function is apparent in FIG. 11.

Figure 12:
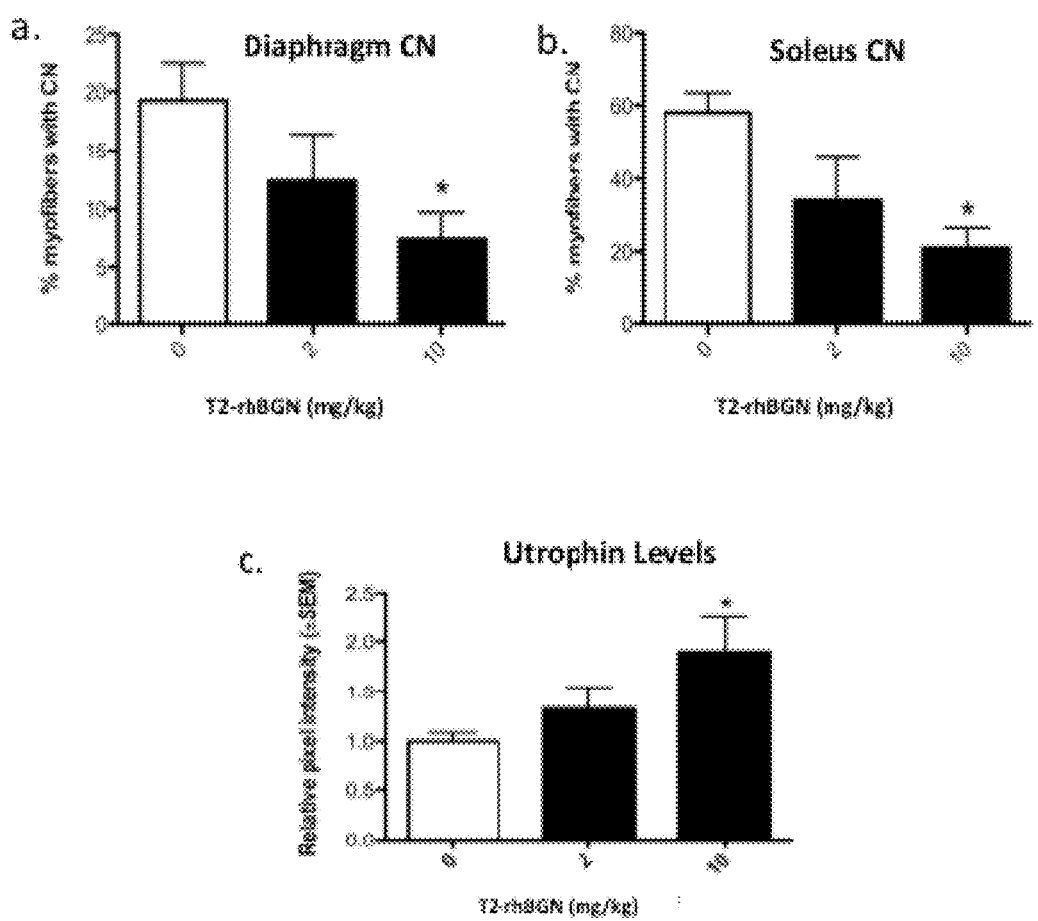
FIG. 12a-c shows the effects of SA-rhBGN on myofibers in vivo. Mdx mice were injected intraperitoneally with vehicle or the indicated doses of SA-rhBGN at P18 and the percentage of myofibers with centrally-localized nuclei were determined for the soleus (b). The same measurement was performed for diaphragm muscles two weeks later (a). Muscle cell membrane levels of utrophin also increased in a dose-dependent manner, measured in the Tibialis Anterior (c). (*p<0.05)

FIG. 12 shows the effects of SA-rhBGN on myofibers in vivo. Mdx mice were injected intraperitoneally with the indicated doses of SA-rhBGN at P18 and the percentage of myofibers with centrally-localized nuclei were determined for the soleus. The same measurement was performed for diaphragm muscles two weeks later. Frozen sections were prepared and stained as previously described (Mercado et al. Faseb J. 2006). Muscle cell membrane levels of utrophin also increased in a dose-dependent manner, measured in the Tibialis Anterior. Sections were observed using a Nikon (Melville, N.Y.) Eclipse E800 microscope and images acquired with Scanalytics IP Lab Spectrum software (Fairfax, Va.) or NIS Elements (Nikon). For scoring the percentage of centrally-localized nuclei, all cross-sectioned myofibers outside of necrosis/regenerative foci in H&E stained sections were counted under a 20× objective.

Example 2: Biglycan Administration Causes an Increase in Collagen VI Levels in a Mouse with Deficient Collagen VI Levels In biglycan null mice with wild-type collagen VI, collagen VI levels are reduced. To test the efficacy of recombinant biglycan to restore collagen VI levels in vivo in this system, a rescue approach was used. Recombinant biglycan was injected intramuscularly into biglycan null mice and the expression of collagen VI was assessed. Purified recombinant non-glycanated biglycan or proteoglycan was injected into the right quadriceps femoris muscles of five week old biglycan null animals (six animals total). Vehicle alone was injected into the left quadriceps to enable intra-animal comparison. In each case the injection site was visualized by the inclusion of 1.0% India ink in the solution. FIG. 13a shows that the injected recombinant biglycan proteoglycan appropriately localizes to the perimysium and epimysium the site of injection.

The injected biglycan had a striking effect on the expression of collagen VI in the biglycan null muscle. By four days post-injection we observed increased collagen VI expression that was tightly colocalized with areas of biglycan staining (FIG. 13b). No upregulation in collagen VI was observed in the vehicle-injected muscle (data not shown). Collagen VI expression was also upregulated by non-glycanated biglycan polypeptide (data not shown). Taken together, these results show that biglycan polypeptide can be delivered to muscle in vivo where it enhances collagen VI expression levels in the interstitium and at the muscle cell surface. Moreover, this rescue can be achieved with either the non-glycanated or proteoglycan forms of biglycan.

Example 3: Purification of S5A-S10A rhBGN

Untagged S5A-S10A rhBGN was purified according to the following scheme. First, frozen aliquots of mutant biglycan were thawed at 4° C. Once completely thawed, these samples were centrifuged to remove any particulate matter. The supernatants were then filtered using a 0.45 μm syringe filter. Filtered sample was then diluted 1:3 with deionized water.

Figure 16:
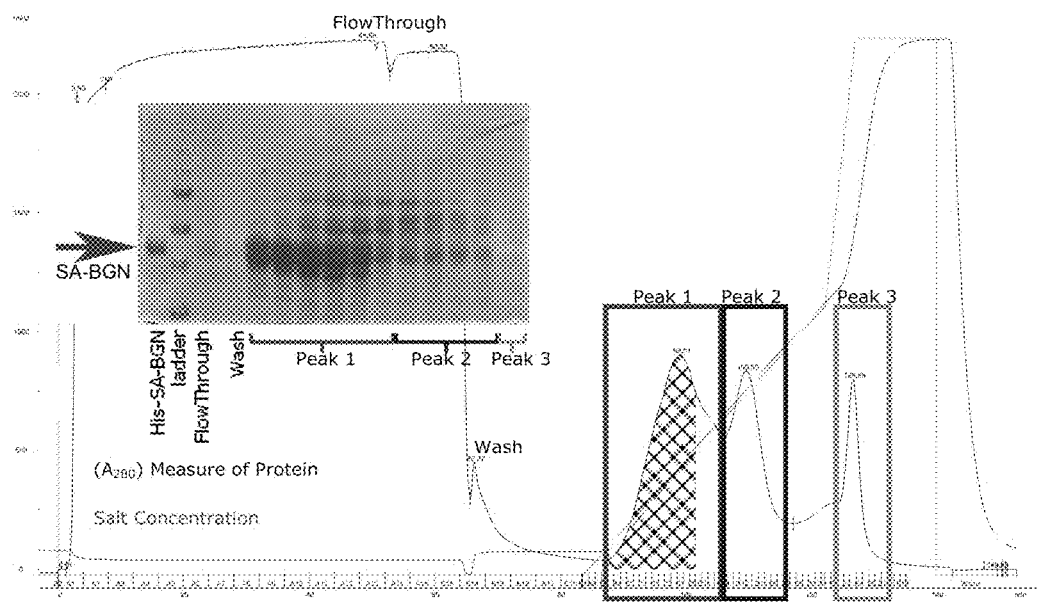
FIG. 16 shows the first step of a protocol for purifying untagged mutant biglycan. In this capture step, an anion exchange column was used. The inset coomassie gel shows that the biglycan eluted in the first peak.

Mutant biglycan was applied to 1 mL HiTrap QFF (GE LifeSciences) anion exchange column at 1 mL/min. The column was initially equilibrated in QFF A buffer (20 mM Tris pH 8.5; 50 mM NaCl). Unbound sample was washed out of the column using QFF A and 4 mL fractions were collected during sample application and wash. Mutant biglycan was eluted in the first portion of a two step gradient (0-50% B over 40 column volumes; 50-100% B over 5 column volumes; QFF B buffer consists of 20 mM Tris pH 8.5; 1 M NaCl). 1 mL fractions were collected and sampled for SDS-PAGE analysis and coomassie staining. Mutant biglycan containing fractions were pooled for the next purification step. FIG. 16 shows the elution profile and coomassie staining obtained for the anion exchange purification step.

Figure 17:
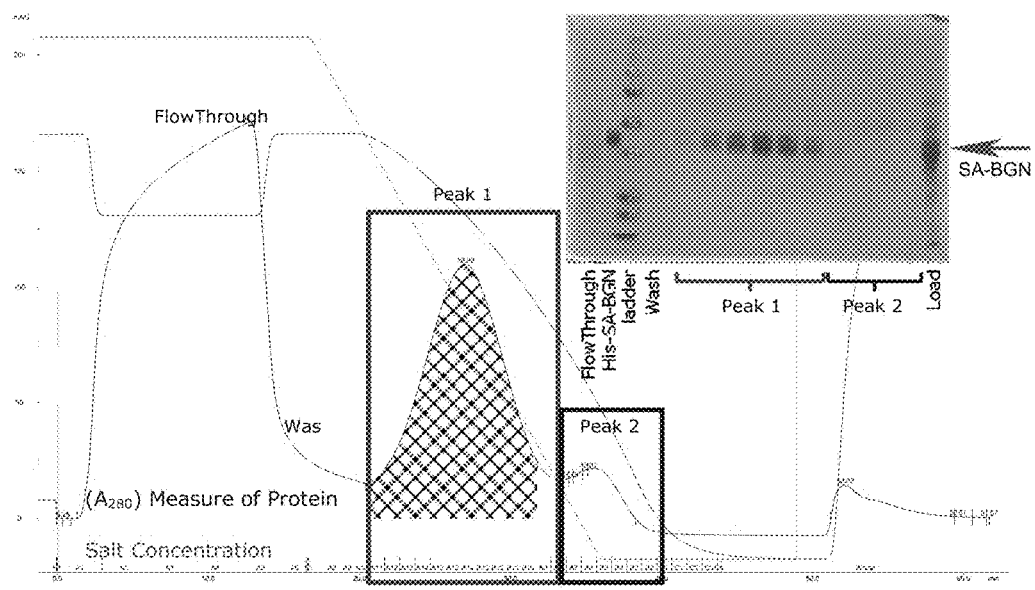
FIG. 17 shows the second step of a protocol for purifying untagged mutant biglycan. This purification step removes bulk impurities using hydrophobic interaction chromatography. The inset coomassie gel shows that the biglycan eluted in the first peak.

Pooled fractions from anion exchange were combined 1:1 with 1 M sodium citrate for a final sodium citrate concentration of 500 mM. Protein was applied to a 1 mL HiTrap ButylS FF (GE LifeSciences) HIC (hydrophobic interaction chromatography) column at 1 mL/min. The column was initially equilibrated in HIC A buffer (20 mM Tris pH 8.5; 200 mM NaCl; 500 mM Sodium Citrate). Unbound sample was washed out of the column using HIC A and 4 mL fractions were collected during sample application and wash. Mutant biglycan was eluted over a 100-0% B gradient over 20 column volumes. (HIC B buffer consists of 20 mM Tris pH 8.5; 200 mM NaCl.) 0.75 mL fractions were collected and sampled for SDS-PAGE analysis and both silver and coomassie staining. FIG. 17 shows the elution profile and coomassie staining obtained for the HIC purification step.

Example 4: Construction of a CHO Line Stably Expressing S5A-S10A rhBGN

A CHO—S cell line was constructed to express untagged S5A-S10A rhBGN using standard protocols. Briefly, rhBGN was inserted into a pCEP4 vector. The vector was transfected into the CHO cells using lipofectamine, and stably transfected cells were isolated using hygromycin selection. This cell line is maintained under conditions that are fully compatible for transfer to the GMP facility and for use in humans.

Figure 18:
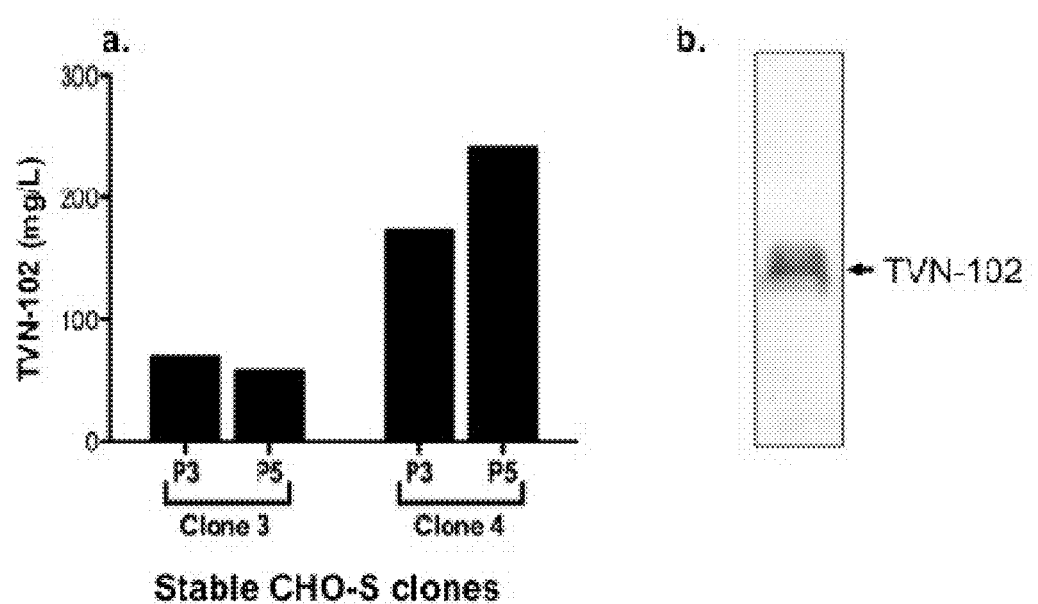
FIGS. 18a and b show the isolation of stable CHO—S clonal cell lines expressing TVN-102 (untagged S5A-S10A rhBGN). (a) Two stable CHO—S cell lines producing TVN-102 at the indicated passages in shake flasks. (b.) Western blot of supernatants from clone 4 showing homogeneity of TVN-102 product.
Figure 19:
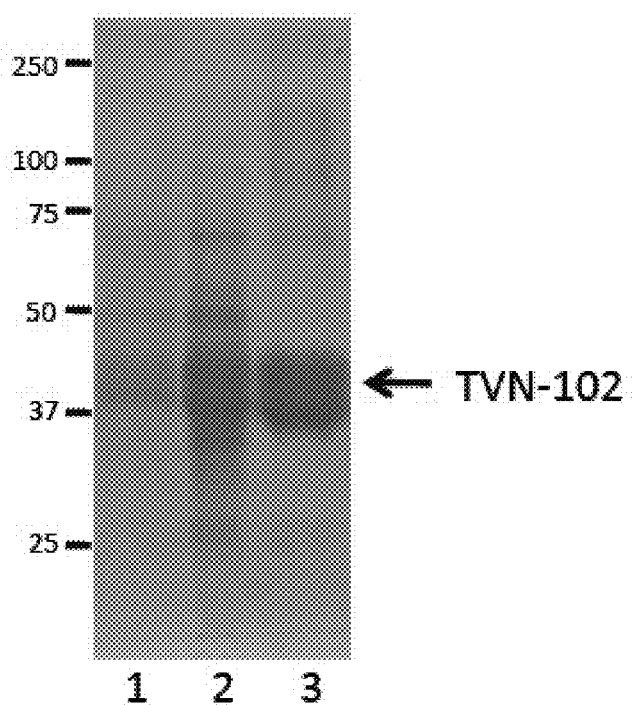
FIG. 19 shows SDS-PAGE analysis of purification of TVN-102 from a CHO—S clonal line. Lane 1: Conditioned medium from a stable CHO—S line expressing TVN-102. Lane 2: Pooled fractions from ion exchange column. Lane 3: Pooled fractions from HIC column Gel stained with Coomassie Blue; 10 µg total protein/lane. Final TVN-102 purity was >90% as judged by Agilent B "GAGs" refers to glycosaminoglycans, used interchangeably herein with "mucopolysaccharides," which are long, unbranched polysaccharide chains composed of repeating disaccharide units. One of the two sugars is always an amino sugar (N-acetylglucosamine or N-acetylgalactosamine). Glycosaminoglycans are covalently linked to a serine residue of a core protein, to form a proteoglycan molecule.
Figure 20:
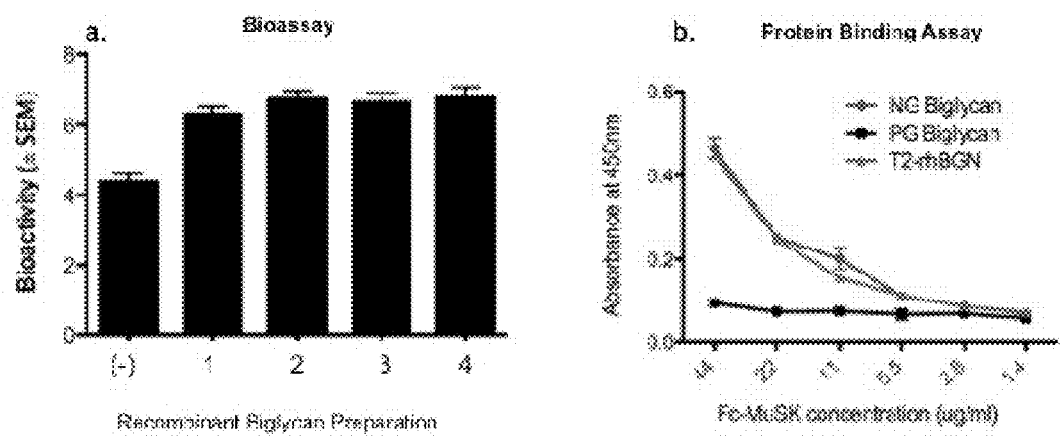

FIG. 18a shows expression of TVN-102 from two stable, clonal cell lines grown in shake flasks. The TVN-102 produced by the cell lines is efficiently secreted and homogeneous (FIG. 18b.). TVN-102 is stable in the media at 37° C. for at least 5 days and bioactivity is retained for at least 2 weeks of storage at 4° C. All chromatography was carried out on an AKTA-100A FPLC. A protein gel of purified TVN-102 is shown in FIG. 19. All resins and methods used are designed to be compatible with regulatory requirements and scale-up and all procedures were performed at room temperature. After two chromatography steps the TVN-102 material is >90% pure as judged by Agilent Bioanalyzer analysis. Mass spectroscopy of the purified material shows that the protein is intact. The material is bioactive as judged by a cell-based agrin potentiation assay (FIG. 20).

Example 5: Protein Binding and Bioactivity Assays for Biglycan

This example shows a cell culture bioassay and a protein binding bioassay to assess the biological activity of the recombinant proteins. Notably, both these assays are selective for the activity of the NG/S5A-S10A forms of recombinant biglycan. The bioassay (FIG. 20a) is based upon the ability of NG or S5A-S10A biglycan to potentiate agrin-induced activity in cultured myotubes. The myotube assay is described above in Example 1 and FIG. 9.

The protein binding assay (FIG. 20b) is based upon the binding of biglycan to the ectodomain of the RTK MuSK. FIG. 20a shows that 4 independent preparations of recombinant biglycan show comparable bioactivity. FIG. 20b shows that both NG and S5A-S10A biglycan bind to MuSK, while recombinant PG biglycan does not. The experiments shown in FIG. 20b were performed as follows. MuSK binding to three different forms of biglycan was tested by ELISA. The indicated biglycan forms were immobilized on plastic and probed with recombinant Fc-fusion ectodomain of MuSK in PBS. Bound Fc-fusion was detected with HRP (horseradish peroxidase)-conjugated anti-mouse secondary antibody (KPL) developed with TMB (tetramethylbenzidine). Absorbances at 450 nm were used to generate the binding curves.

EQUIVALENTS

Those skilled in the art will recognize, or be able to ascertain using no more than routine experimentation, many equivalents of the specific embodiments of the invention described herein. Such equivalents are intended to be encompassed by the following claims.

We claim:

1. A method for treating a muscular dystrophy in a subject, comprising administering to the subject an effective amount of a biglycan-related polypeptide comprising an amino acid sequence corresponding to amino acids 38-365 of SEQ ID NO: 11, which biglycan-related polypeptide comprises less than 1% total carbohydrate by weight.

2. The method of claim 1, wherein the muscular dystrophy is selected from Duchenne's Muscular Dystrophy, Becker's Muscular Dystrophy, Congenital Muscular Dystrophy, Limb-girdle Muscular Dystrophy, and myotonic dystrophy.

3. A method for treating amyotrophic lateral sclerosis in a subject, comprising administering to the subject an effective amount of a biglycan-related polypeptide comprising an amino acid sequence corresponding to amino acids 38-365 of SEQ ID NO: 11, which biglycan-related polypeptide comprises less than 1% total carbohydrate by weight.

4. A method for treating Bethlem's myopathy, Ullrich Congenital Muscular Dystrophy, or Sorsby's fundus dystrophy, comprising administering to the subject an effective amount of a biglycan-related polypeptide comprising an amino acid sequence corresponding to amino acids 38-365 of SEQ ID NO: 11, which biglycan-related polypeptide comprises less than 1% total carbohydrate by weight.

* * * * *